(12) United States Patent
Han et al.

(10) Patent No.: US 9,790,463 B2
(45) Date of Patent: *Oct. 17, 2017

(54) **CULTURING MEDIUM AND METHOD FOR CULTURING A BACTERIUM OF GENUS *TEPIDIMONAS***

(71) Applicant: INDUSTRIAL TECHNOLOGY RESEARCH INSTITUTE, Chutung, Hsinchu (TW)

(72) Inventors: Yin-Lung Han, Tainan (TW); Tai-Rong Guo, Zhubei (TW); Jo-Shu Chang, Taichung (TW); Yung-Chong Lou, Tainan (TW); Chieh-Lun Cheng, Bade (TW); Wan-Ju Yu, Tainan (TW); Chih-Hsi Liu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 196 days.

This patent is subject to a terminal disclaimer.

(21) Appl. No.: 14/229,596

(22) Filed: Mar. 28, 2014

(65) Prior Publication Data

US 2015/0184121 A1 Jul. 2, 2015

(30) Foreign Application Priority Data

Dec. 26, 2013 (TW) .............................. 102148375 A

(51) Int. Cl.
*C12N 1/20* (2006.01)

(52) U.S. Cl.
CPC ....................................... *C12N 1/20* (2013.01)

(58) Field of Classification Search
None
See application file for complete search history.

(56) References Cited

U.S. PATENT DOCUMENTS

| | | | |
|---|---|---|---|
| 7,695,834 | B1 | 4/2010 | Borole |
| 8,426,566 | B2 | 4/2013 | Shaw et al. |
| 2012/0277322 | A1 | 11/2012 | Di Maiuta et al. |
| 2013/0189763 | A1* | 7/2013 | Dalla-Betta ............ C12M 29/02 435/252.1 |

FOREIGN PATENT DOCUMENTS

| | | | |
|---|---|---|---|
| CN | 102628025 A | | 8/2012 |
| CN | 103204589 A | * | 7/2013 |
| CN | 103215213 A | * | 7/2013 |
| TW | 201328597 A1 | | 7/2013 |

OTHER PUBLICATIONS

Zinder, Stephen H., and Markus Koch. "Non-aceticlastic methanogenesis from acetate: acetate oxidation by a thermophilic syntrophic coculture." Archives of Microbiology 138.3 (1984): 263-272.*
Zeikus, J. G., et al. "Bacterial methanogenesis: acetate as a methane precursor in pure culture." Archives of Microbiology 104.1 (1975): 129-134.*
Zeikus, J. G. "The biology of methanogenic bacteria." Bacteriological reviews 41.2 (1977): 514.*
Grant, C. L., and David Pramer. "Minor element composition of yeast extract." Journal of bacteriology 84.4 (1962): 869.*
Zeikus, J. G., et al. "Oxidoreductases involved in cell carbon synthesis of Methanobacterium thermoautotrophicum." Journal of Bacteriology 132.2 (1977): 604-613.*
Degryse et al., "A Comparative Analysis of Extreme Thermophilic Bacteria Belonging to the Genus *Thermus*", Archives of Microbiology, vol. 117, 1978, pp. 189-196.
Taiwanese Office Action and Search Report, dated Dec. 25, 2014, for Taiwanese Application No. 102148375.
Albuquerque et al., "*Tepidimonas thermarum* sp. nov., a new slightly thermophilic betaproteobacterium isolated from the Elisenquelle in Aachen and emended description of the genus *Tepidimonas*", Systematic and Applied Microbiology, vol. 29, 2006, pp. 450-456.
Chen et al., "*Tepidimonas fonticaldi* sp. nov., a slightly thermophilic betaproteobacterium isolated from a hot spring", International Journal of Systematic and Evolutionary Microbiology, vol. 63, 2013, pp. 1810-1816.
Chen et al., "*Tepidimonas taiwanensis* sp. nov., a novel alkaline-protease-producing bacterium isolated from a hot spring", Extremophiles, vol. 10, 2006, pp. 35-40.
DSMZ GmbH, "27. Rhodospirillaceae Medium (modified)", Microogranisms, 2007, pp. 1-2.
Moreira et al., "*Tepidimonas ignava* gen. nov., sp. nov., a new chemolithoheterotrophic and slightly thermophilic member of the B-Proteobacteria", International Journal of Systematic and Evolutionary Microbiology, vol. 50, 2000, pp. 735-742.

* cited by examiner

*Primary Examiner* — Robert Yamasaki
(74) *Attorney, Agent, or Firm* — Birch, Stewart, Kolasch & Birch, LLP

(57) ABSTRACT

The disclosure provides a culturing medium for culturing a bacterium of genus *Tepidimonas*, including: a carbon source which is an organic acid, selected from a group consisting of acetate, lactate and butyrate; a nitrogen source selected from a group consisting of ammonium sulfate (($NH_4$)$_2SO_4$), ammonium nitrate ($NH_4NO_3$), ammonium chloride ($NH_4Cl$) and urea; phosphate; magnesium chloride ($MgCl_2$); yeast extract; and trace elements.

29 Claims, 16 Drawing Sheets

US 9,790,463 B2

CULTURING MEDIUM AND METHOD FOR CULTURING A BACTERIUM OF GENUS *TEPIDIMONAS*

CROSS REFERENCE TO RELATED APPLICATION

The present application is based on, and claims priority from, Taiwan Application Serial Number 102148375, filed on Dec. 26, 2013, the disclosure of which is hereby incorporated by reference herein in its entirety.

TECHNICAL FIELD

The technical field relates to a culturing medium and a method for culturing a bacterium of genus *Tepidimonas*.

BACKGROUND

Bacteria of genus *Tepidimonas* are bacteria which are gram-negative, strictly aerobic, oxidase- and catalase-positive, rod-shaped and slightly thermophilic bacteria.

The inventors of the present disclosure anteriorly sampled the water samples of An-tong hot spring in Hualien County, Taiwan. Then, bacterial strains in the water samples were isolated and purified to obtain a novel bacterium of *Tepidimonas* named *Tepidimonas fonticaldi* sp. nov. Extracellular proteins secreted by *Tepidimonas fonticaldi* sp. nov. have excellent effects for binding metal ions, and are not influenced by environmental conditions, such as high temperature, high pressure, or pH value. Therefore, the extracellular proteins secreted by *Tepidimonas fonticaldi* sp. nov. can prevent metal salt scale, especially calcium carbonate, formed in boiler equipment, underground pipelines, geothermal wells, industrial wastewater or hard water, to keep the function of the machines and reduce the operating time and cost.

However, the growth and self-protein metabolizing rate of bacteria of genus *Tepidimonas* are slow and it causes that the protein is hard to be obtained. Therefore, a novel culturing medium and a novel culturing method are needed.

SUMMARY

The disclosure provides a culturing medium for culturing a bacterium of genus *Tepidimonas*, comprising: a carbon source which is an organic acid, selected from a group consisting of acetate, lactate and butyrate; a nitrogen source selected from a group consisting of ammonium sulfate (($NH_4$)$_2SO_4$), ammonium nitrate ($NH_4NO_3$), ammonium chloride ($NH_4Cl$) and urea; phosphate; magnesium chloride ($MgCl_2$); yeast extract; and trace elements.

The disclosure further provides a method for culturing a bacterium of genus *Tepidimonas*, comprising: culturing a bacterium of genus *Tepidimonas* with a culturing medium, wherein the culturing medium comprises: a carbon source which is an organic acid, selected from a group consisting of acetate, lactate and butyrate; a nitrogen source selected from a group consisting of ammonium sulfate (($NH_4$)$_2SO_4$), ammonium nitrate ($NH_4NO_3$), ammonium chloride ($NH_4Cl$) and urea; a phosphate; magnesium chloride ($MgCl_2$); a yeast extract; and trace elements.

A detailed description is given in the following embodiments with reference to the accompanying drawings.

BRIEF DESCRIPTION OF DRAWINGS

The disclosure can be more fully understood by reading the subsequent detailed description and examples with references made to the accompanying drawings, wherein.

DETAILED DESCRIPTION

Figure 1A:
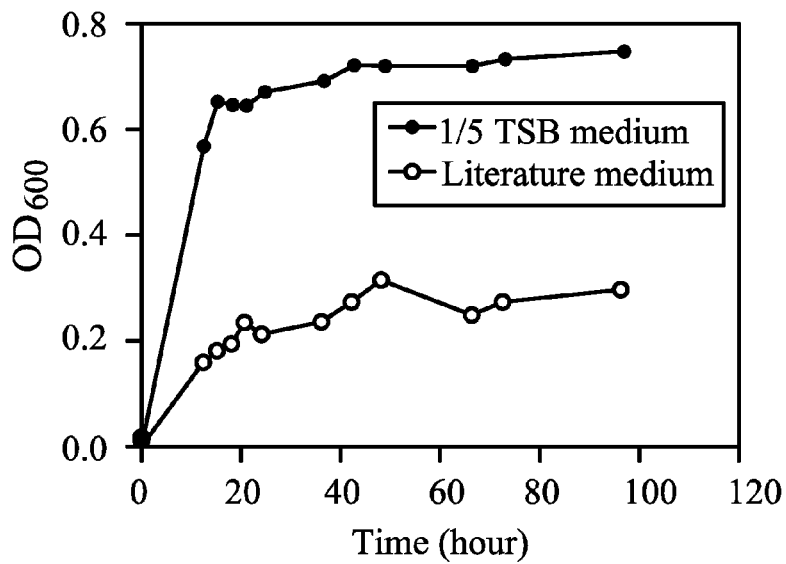
FIGS. 1A, 1B and 1C respectively show the optical densities ($OD_{600}$), pH values, and protein concentration of the bacterial suspension determined at different time points at a condition of culturing *Tepidimonas fonticaldi* sp. nov. KCTC 12528BP by the 1/5-TSB medium or the literature medium.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

In one embodiment of the present disclosure, the present disclosure provides a culturing medium for culturing a bacterium of genus *Tepidimonas*.

The culturing medium for culturing a bacterium of genus *Tepidimonas* of the present disclosure may comprise, but is not limited to, a carbon source, a nitrogen source, phosphate, magnesium chloride ($MgCl_2$), yeast extract and trace elements.

In the culturing medium for culturing a bacterium of genus *Tepidimonas* of the present disclosure, the above-mentioned carbon source is an organic acid, and examples of the above-mentioned organic acid may comprise, but are not limited to, acetate, lactate, butyrate, etc. In one embodiment, the above-mentioned carbon source may be acetate.

Moreover, in the culturing medium for culturing a bacterium of genus *Tepidimonas* of the present disclosure, examples of the above-mentioned nitrogen source may comprise ammonium sulfate (($NH_4)_2SO_4$), ammonium nitrate ($NH_4NO_3$), ammonium chloride ($NH_4Cl$), urea, etc., but is not limited thereto. In one embodiment, the above-mentioned nitrogen source may be ammonium sulfate (($NH_4)_2SO_4$).

In the culturing medium for culturing a bacterium of genus *Tepidimonas* of the present disclosure, examples of suitable phosphate may comprise, but is not limited to, disodium hydrogen phosphate ($Na_2HPO_4$), potassium dihydrogen phosphate ($KH_2PO_4$), sodium dihydrogen phosphate ($NaH_2PO_4$), dipotassium phosphate ($K_2HPO_4$), etc. or any combination thereof.

In one embodiment, the foregoing phosphate in the culturing medium for culturing a bacterium of genus *Tepidimonas* of the present disclosure may comprise disodium hydrogen phosphate ($Na_2HPO_4$) and dipotassium phosphate ($K_2HPO_4$). In another embodiment, the foregoing phosphate in the culturing medium for culturing a bacterium of genus *Tepidimonas* of the present disclosure may only comprise dipotassium phosphate ($K_2HPO_4$), and in this embodiment, the culturing medium for culturing a bacterium of genus *Tepidimonas* of the present disclosure may further comprise a carbonate, such as sodium bicarbonate ($NaHCO_3$).

Furthermore, in the culturing medium for culturing a bacterium of genus *Tepidimonas* of the present disclosure, the trace elements may comprise, for example, zinc (Zn), manganese (Mn), boron (B), cobalt (Co), copper (Cu), nickel (Ni), molybdenum (Mo), etc, but is not limited thereto. In one embodiment, the preceding trace elements in the culturing medium of the present disclosure may comprise zinc, manganese, boron, cobalt, copper, nickel and molybdenum. In this embodiment, the respective element may be in the forms shown in the following, but is not limited thereto: zinc may be in the form of zinc sulfate ($ZnSO_4$), manganese may be in the form of manganese chloride ($MnCl_2$), boron may be in the form of boric acid ($H_3BO_3$), cobalt may be in the form of cobalt chloride ($CoCl_2$), copper may be in the form of copper chloride ($CuCl_2$), Ni may be in the form of nickel chloride ($NiCl_2$), and Mo is sodium molybdate ($Na_2MoO_4$).

In addition, in the culturing medium of the present disclosure, the content of the carbon source may be about 0.2 g/L-10 g/L, the content of the nitrogen source may be about 0.2 g/L-10 g/L, the content of the phosphate may be about 0.2 g/L-25 g/L, the content of the $MgCl_2$ may be about 0.01 g/L-5 g/L, the content of the yeast extract may be about 0.2 g/L-15 g/L, and the content of the trace elements may be about 0.01 g/L-1 g/L.

In the culturing medium for culturing a bacterium of genus *Tepidimonas* of the present disclosure, the carbon-nitrogen weight ratio of the carbon source to the nitrogen source may be about 1-40, and in another embodiment, the carbon-nitrogen weight ratio of the carbon source to the nitrogen source may be about 1-20.

The preceding culturing medium for culturing a bacterium of genus *Tepidimonas* of the present disclosure is suited to culture any bacterium of genus *Tepidimonas*. Examples of the bacterium of genus *Tepidimonas* mentioned above may comprise, but are not limited to *Tepidimonas fonticaldi, Tepidimonas ignava, Tepidimonas aquatic, Tepidimonas taiwanesis*, etc.

In one embodiment, the preceding culturing medium for culturing a bacterium of genus *Tepidimonas* of the present disclosure is suited to culture *Tepidimonas fonticaldi*. The *Tepidimonas fonticaldi* may be *Tepidimonas fonticaldi* sp. nov. which was deposited at the Korean Collection for Type Cultures (KCTC) on Dec. 4, 2013, and the deposit number of which is KCTC 12528BP. The *Tepidimonas fonticaldi* sp. nov. KCTC 12528BP is capable of secreting extracellular proteins. By culturing with the culturing medium of the present disclosure, the *Tepidimonas fonticaldi* sp. nov. KCTC 12528BP is capable of secreting extracellular proteins.

Furthermore, in one embodiment in which the culturing medium for culturing a bacterium of genus *Tepidimonas* of the present disclosure is suited to culture *Tepidimonas fonticaldi* sp. nov. KCTC 12528BP, the carbon source of the culturing medium for culturing a bacterium of genus *Tepidimonas* of the present disclosure may be acetate, and the nitrogen source of that may be ammonium sulfate (($NH_4$)$_2SO_4$).

In addition, for this culturing medium, in one specific embodiment, the content of the acetate may be about 0.2 g/L-5 g/L, the content of the ammonium sulfate may be about 0.4 g/L-3 g/L, the content of the phosphate may be about 1 g/L-12 g/L, the content of the $MgCl_2$ may be about 0.01 g/L-0.5 g/L, the content of the yeast extract may be about 0.2 g/L-5 g/L, and the content of the trace elements may be about 0.01 g/L-0.3 g/L.

For the specific embodiment mentioned above, the phosphate of the culturing medium may comprise disodium hydrogen phosphate ($Na_2HPO_4$) and dipotassium phosphate ($K_2HPO_4$). Or, for the specific embodiment mentioned above, the phosphate of the culturing medium may only comprise dipotassium phosphate ($K_2HPO_4$), and the culturing medium further comprises sodium bicarbonate ($NaHCO_3$).

Moreover, for the specific embodiment mentioned above, the trace elements of the culturing medium may comprise zinc (Zn), manganese (Mn), boron (B), cobalt (Co), copper (Cu), nickel (Ni) and molybdenum (Mo). In addition, the respective element may be in the forms shown in the following, but is not limited thereto: zinc may be in the form of zinc sulfate ($ZnSO_4$), manganese may be in the form of manganese chloride ($MnCl_2$), boron may be in the form of boric acid ($H_3BO_3$), cobalt may be in the form of cobalt chloride ($CoCl_2$), copper may be in the form of copper chloride ($CuCl_2$), Ni may be in the form of nickel chloride ($NiCl_2$), and Mo is sodium molybdate ($Na_2MoO_4$).

Furthermore, for the specific embodiment mentioned above, the carbon-nitrogen weight ratio of the carbon source to the nitrogen source may be about 1-20, or may be about 11.

In another embodiment of the present disclosure, the present disclosure provides a method for culturing a bacterium of genus *Tepidimonas*.

The method for culturing a bacterium of genus *Tepidimonas* of the present disclosure may comprise the following step, but it is not limited thereto.

A bacterium of genus *Tepidimonas* is cultured with a culturing medium, wherein the culturing medium may comprise, but is not limited to, a carbon source, a nitrogen source, phosphate, magnesium chloride ($MgCl_2$), yeast extract and trace elements. Moreover, the above-mentioned carbon source is an organic acid, and examples of the above-mentioned organic acid may comprise, but are not limited to acetate, lactate, and butyrate, etc. In one embodiment, the above-mentioned carbon source may be acetate. Moreover, examples of the above-mentioned nitrogen source may comprise ammonium sulfate (($NH_4$)$_2SO_4$), ammonium nitrate ($NH_4NO_3$), ammonium chloride ($NH_4Cl$) and urea, etc., but they are not limited thereto. In one embodiment, the above-mentioned nitrogen source may be ammonium sulfate (($NH_4$)$_2SO_4$).

In the foregoing method for culturing a bacterium of genus *Tepidimonas* of the present disclosure, the bacterium of genus *Tepidimonas* is cultured at about 30-70° C. In one embodiment, the bacterium of genus *Tepidimonas* is cultured at about 30-60° C.

In the foregoing method for culturing a bacterium of genus *Tepidimonas* of the present disclosure, the bacterium of genus *Tepidimonas* is cultured at pH 5-pH 9. In one embodiment, the bacterium of genus *Tepidimonas* is cultured at pH 6-pH 9.

In the foregoing method for culturing a bacterium of genus *Tepidimonas* of the present disclosure, the bacterium of genus *Tepidimonas* is cultured under a stirring rate of about 0-500 rpm. In one embodiment, the bacterium of genus *Tepidimonas* is cultured under a stirring rate of about 0-200 rpm.

In the foregoing method for culturing a bacterium of genus *Tepidimonas* of the present disclosure, the time for culturing the bacterium of genus *Tepidimonas* is about 12-120 hours. In one embodiment, the time for culturing the bacterium of genus *Tepidimonas* is about 46-120 hours.

In the culturing medium used by the method for culturing a bacterium of genus *Tepidimonas* of the present disclosure mentioned above, examples of suitable phosphate may comprise, but are not limited to, disodium hydrogen phosphate ($Na_2HPO_4$), potassium dihydrogen phosphate ($KH_2PO_4$), sodium dihydrogen phosphate ($NaH_2PO_4$), dipotassium phosphate ($K_2HPO_4$), etc. and any combination thereof.

In one embodiment, the foregoing phosphate in the culturing medium of the present disclosure may comprise disodium hydrogen phosphate ($Na_2HPO_4$) and dipotassium phosphate ($K_2HPO_4$). In another embodiment, the foregoing phosphate in the culturing medium of the present disclosure may only comprise dipotassium phosphate ($K_2HPO_4$), and in this embodiment, the culturing medium of the present disclosure may further comprise a carbonate, such as sodium bicarbonate ($NaHCO_3$).

Furthermore, in the culturing medium used by the method for culturing a bacterium of genus *Tepidimonas* of the present disclosure mentioned above, the trace elements may comprise, for example, zinc (Zn), manganese (Mn), boron (B), cobalt (Co), copper (Cu), nickel (Ni), molybdenum (Mo), etc., but is not limited thereto. In one embodiment, the preceding trace elements in the culturing medium of the present disclosure may comprise zinc, manganese, boron, cobalt, copper, nickel and molybdenum. In this embodiment, the respective element may be in the forms shown in the following, but is not limited thereto: zinc may be in the form of zinc sulfate ($ZnSO_4$), manganese may be in the form of manganese chloride ($MnCl_2$), boron may be in the form of boric acid ($H_3BO_3$), cobalt may be in the form of cobalt chloride ($CoCl_2$), copper may be in the form of copper chloride ($CuCl_2$), Ni may be in the form of nickel chloride ($NiCl_2$), and Mo is sodium molybdate ($Na_2MoO_4$).

In addition, in the culturing medium used by the method for culturing a bacterium of genus *Tepidimonas* of the present disclosure mentioned above, the content of the carbon source may be about 0.2 g/L-10 g/L, the content of the nitrogen source may be about 0.2 g/L-10 g/L, the content of the phosphate may be about 0.2 g/L-25 g/L, the content of the $MgCl_2$ may be about 0.01 g/L-5 g/L, the content of the yeast extract may be about 0.2 g/L-15 g/L, and the content of the trace elements may be about 0.01 g/L-1 g/L.

In the culturing medium used by the method for culturing a bacterium of genus *Tepidimonas* of the present disclosure mentioned above, the carbon-nitrogen weight ratio of the carbon source to the nitrogen source may be about 1-40, and in another embodiment, the carbon-nitrogen weight ratio of the carbon source to the nitrogen source may be about 1-20.

The bacterium of genus *Tepidimonas* cultured by the method for culturing a bacterium of genus *Tepidimonas* of the present disclosure mentioned above may be any bacterium of genus *Tepidimonas*. Examples of the bacterium of genus *Tepidimonas* mentioned above may comprise, but is not limited to, *Tepidimonas fonticaldi, Tepidimonas ignava, Tepidimonas aquatic, Tepidimonas taiwanesis*, etc.

In one embodiment, the bacterium of genus *Tepidimonas* cultured by the method for culturing a bacterium of genus *Tepidimonas* of the present disclosure mentioned above may be *Tepidimonas fonticaldi*. The *Tepidimonas fonticaldi* may be *Tepidimonas fonticaldi* sp. nov. which was deposited at the Korean Collection for Type Cultures (KCTC) on Dec. 4, 2013, and the deposit number of which is KCTC 12528BP. The *Tepidimonas fonticaldi* sp. nov. KCTC 12528BP is capable of secreting extracellular proteins. By culturing with the culturing medium of the present disclosure, the *Tepidimonas fonticaldi* sp. nov. KCTC 12528BP is capable of secreting extracellular proteins.

Furthermore, in one embodiment in which the bacterium of genus *Tepidimonas* cultured by the method for culturing a bacterium of genus *Tepidimonas* of the present disclosure mentioned above is *Tepidimonas fonticaldi* sp. nov. KCTC 12528BP, in the culturing medium used by the method of the present disclosure, the carbon source may be acetate, and the nitrogen source may be ammonium sulfate (($NH_4$)$_2SO_4$).

In addition, for the foregoing method for culturing *Tepidimonas fonticaldi* sp. nov. KCTC 12528BP of the present disclosure, in one specific embodiment, in the culturing medium used by this method, the content of the acetate may be about 0.2 g/L-5 g/L, the content of the ammonium sulfate may be about 0.4 g/L-3 g/L, the content of the phosphate may be about 1 g/L-12 g/L, the content of the $MgCl_2$ may be about 0.01 g/L-0.5 g/L, the content of the yeast extract may be about 0.2 g/L-5 g/L, and the content of the trace elements may be about 0.01 g/L-0.3 g/L.

In the preceding specific embodiment, in the culturing medium used by this method, the phosphate of the culturing medium may comprise disodium hydrogen phosphate ($Na_2HPO_4$) and dipotassium phosphate ($K_2HPO_4$). Or, for the specific embodiment mentioned above, the phosphate of the culturing medium may only comprise dipotassium phosphate ($K_2HPO_4$), and the culturing medium further comprises sodium bicarbonate ($NaHCO_3$).

Moreover, for the specific embodiment mentioned above, the trace elements of the culturing medium may comprise zinc (Zn), manganese (Mn), boron (B), cobalt (Co), copper (Cu), nickel (Ni) and molybdenum (Mo). In addition, the respective element may be in the forms shown in the following, but is not limited thereto: zinc may be in the form of zinc sulfate ($ZnSO_4$), manganese may be in the form of manganese chloride ($MnCl_2$), boron may be in the form of boric acid ($H_3BO_3$), cobalt may be in the form of cobalt chloride ($CoCl_2$), copper may be in the form of copper chloride ($CuCl_2$), Ni may be in the form of nickel chloride ($NiCl_2$), and Mo is sodium molybdate ($Na_2MoO_4$).

Furthermore, for the specific embodiment mentioned above, the carbon-nitrogen weight ratio of the carbon source to the nitrogen source may be about 1-20, or may be about 11.

In the specific embodiment mentioned above, the bacterium of genus *Tepidimonas* is cultured at about 30-60° C., for example, 55° C.

Moreover, in the specific embodiment mentioned above, the bacterium of genus *Tepidimonas* is cultured pH 6-pH 9, for example, pH 7 or pH 8.

In addition, for the specific embodiment mentioned above, in the method of the present disclosure, the bacterium of genus *Tepidimonas* is cultured under a stirring rate of about 0-200 rpm, for example, 200 rpm.

Furthermore, in the specific embodiment mentioned above, the time for culturing the bacterium of genus *Tepidimonas* is about 46-120 hours.

Examples

1. Experimental Materials and Methods 1.1 Activation and Enrichment Culture for Bacterial Strains

*Tepidimonas fonticaldi* sp. nov. KCTC 12528BP, *Tepidimonas ignava* (purchased from Deutsche Sammlung von Mikroorganismen und Zellkulturen, DSMZ, catalog number SPS-1037) and *Tepidimonas aquatic* (purchased from Deutsche Sammlung von Mikroorganismen und Zellkulturen, DSMZ, catalog number CLN-1) in the frozen vials were scraped out by sterilized loops, and then added into 3 mL 1/5-TSB (Tryptocase Soy Broth) (the detailed ingredients shown in the following Table 1) liquid culturing medium, and cultured at 55° C. and under a stirring rate of 200 rpm for 1-2 days for activation. After the activation of bacterial strains is completed, 1 mL of the activated bacterial strains were added to 100 mL experimental culturing medium, and cultured under a stirring rate of 200 rpm and at 55° C. for 3-5 days for enrichment, and so that the subsequent experiments could proceed.

TABLE 1

Ingredients for 1/5-TSB medium

| Ingredients | Content (g/L) |
| --- | --- |
| Pancreatic digest of casein | 3.40 |
| Enzymatic digest of soybean meal | 0.60 |
| Dextrose | 0.50 |
| Sodium chloride | 1.00 |
| Dipotassium phosphate | 0.50 |

1.2 Establishment of Bacterial Strain Culturing Environment and Composition of Culturing Medium In this experiment, based on different experimental designs, optimum growth environmental factors and culturing medium composition for the target bacterial strains were determined, to effectively raise the concentrations of the bacterial cell or to further promote the protein secreting rate for the bacterial cells.

1.2.1 Tests for Known Culturing Medium

The testing bacterial strain was cultured by a 1/5-TSB medium and a medium which is used to culture *Tepidimonas thermarum* sp. nov., disclosed in Albuquerquea et al., 2006 (Albuquerquea L., Tiagob I., Veri'ssimob A. and da Costaa M. S., 2006, *Tepidimonas thermarum* sp. nov., a new slightly thermophilic betaproteobacterium isolated from the Elisenquelle in Aachen and emended description of the genus *Tepidimonas*. Systematic and Applied Microbiology 29: 450-456) (hereinafter called literature medium). The ingredients for the literature medium are shown in the following Table 2.

TABLE 2

Ingredients for the literature medium

| Ingredients | Content (g/L) |
| --- | --- |
| $Na_2HPO_4 \cdot 12H_2O$ | 10.60 |
| $KH_2PO_4$ | 1.50 |

TABLE 2-continued

Ingredients for the literature medium

| | Content (g/L) |
|---|---|
| NH₄Cl | 0.30 |
| Yeast extract | 1.00 |
| MgCl₂ | 0.10 |
| Trace element solution | 1 ml/L |
| (Ingredients thereof are shown as below) | |
| Trace element solution | |
| ZnSO₄•7H₂O | 0.10 |
| MnCl₂•4H₂O | 0.03 |
| H₃BO₃ | 0.30 |
| CoCl₂•6H₂O | 0.20 |
| CuCl₂•2H₂O | 0.01 |
| NiCl₂•6H₂O | 0.02 |
| Na₂MoO₄•2H₂O | 0.03 |

1.2.2 Determination of Suitable Culturing Conditions

A. Test for Environmental Factors

By using the preceding literature medium as the culturing medium, the testing bacterial strain was cultured under various culturing temperatures, initial culturing pH values, and culturing stirring speeds to determine suitable culturing temperatures, initial pH values and stirring rates. The methods for the tests are shown as follows.

(1) Test for Culturing Temperatures

Under a stirring rate of 200 rpm and without controlling the initial pH value, the testing bacterial strain was cultured at temperatures of 50° C., 55° C., 60° C., 65° C. or 70° C.

(2) Investigation for Initial pH Value

After the optimum culturing temperature was determined, at this optimum temperature, under a stirring rate of 200 rpm, the testing bacterial strain was cultured at pH 5.0, pH 6.0, pH 7.0, pH 8.0 or pH 9.0.

(3) Test for Stirring Rate

After the optimum culturing temperature and initial pH value were determined, at the optimum temperature and initial pH value, the testing bacterial strain was cultured under stirring rates of 0 rpm, 100 rpm or 200 rpm.

B. Test for Composition of the Culturing Medium

The literature medium was used as a base for a modified medium, and a part of the ingredients (including carbon source, nitrogen source, etc.) therein was added, deleted and/or replaced to form various modified mediums. After that, the testing bacterial strain was cultured by modified mediums having various carbon sources, nitrogen sources, carbon source concentrations, nitrogen source concentrations and carbon-nitrogen ratio, to obtain suitable culturing mediums.

(1) Test for Carbon Sources

The literature medium was used as a base for a modified medium, and glucose, sucrose, starch, acetate, lactase or butyrate used as the carbon source was added to the literature medium to respectively form different modified mediums containing different carbon sources. After that, the testing bacterial strain was cultured by the different modified mediums containing different carbon sources, to determine suitable carbon sources.

(2) Test for Nitrogen Sources

The literature medium was used as a base for a modified medium, and the nitrogen source in the literature medium was replaced with ammonium sulfate ((NH₄)₂SO₄), ammonium nitrate (NH₄NO₃) or urea or without replacement (ammonium chloride (NH₄Cl)) to respectively form different modified mediums containing different nitrogen sources. After that, the testing bacterial strain was cultured by the different modified mediums containing different nitrogen sources, to determine suitable nitrogen sources.

(3) Test for Carbon Source Concentrations

The literature medium was used as a base for a modified medium, and a suitable carbon source determined in the above test was added to the literature medium by different addition amounts to form different modified mediums with different carbon source concentrations. After that, the testing bacterial strain was cultured by the different modified mediums with different carbon source concentrations, to determine a suitable range for the carbon source.

(4) Test for Nitrogen Source Concentrations

The literature medium was used as a base for a modified medium, and a suitable nitrogen source determined in the above test (which was used to replace the nitrogen source present in the literature medium) was added to the literature medium in different addition amounts to form different modified mediums with different nitrogen source concentrations. After that, the testing bacterial strain was cultured by the different modified mediums with different nitrogen source concentrations, to determine a suitable range for the nitrogen source.

(5) Test for Carbon-Nitrogen Ratios

The literature medium was used as a base for a modified medium, and a suitable carbon source and a nitrogen source (which is used to replace the nitrogen source present in the literature medium) determined in the above tests were added to the literature medium by different carbon-nitrogen weight ratios to form different modified mediums with different carbon-nitrogen weight ratios. After that, the testing bacterial strain was cultured by the different modified mediums with different carbon-nitrogen weight ratios, to determine a suitable range for the carbon-nitrogen weight ratio.

(6) Test for Replacing Na₂HPO₄.12H₂O with NaHCO₃

The literature medium was used as a base for a modified medium, a suitable carbon source and a nitrogen source (which is used to replace the nitrogen source present in the literature medium) determined in the above tests were added to the literature medium by a suitable addition amount and weight ratio, and Na₂HPO₄.12H₂O was replaced with NaHCO₃ or not to form a modified medium containing Na₂HPO₄ and a modified medium containing NaHCO₃. After that, the testing bacterial strain was cultured by the two modified mediums mentioned above to estimate the feasibility of replacing Na₂HPO₄.12H₂O with NaHCO₃.

(7) Test for Yeast Extract

The literature medium was used as a base for a modified medium, a suitable carbon source and a nitrogen source (which is used to replace the nitrogen source present in the literature medium) determined in the above tests were added to the literature medium by a suitable addition amount and weight ratio, and the yeast extract therein was deleted or not deleted to form a modified medium with the yeast extract and a modified medium without the yeast extract. After that, the testing bacterial strain was cultured by the two modified mediums mentioned above to estimate whether the yeast extract was necessary or not.

1.2.3 Application Scope Tests for the Culturing Medium

A. Test for Culturing Temperatures

According to a suitable culturing medium formula determined by the foregoing tests, a suitable culturing medium was prepared. After that, by using this suitable culturing medium, under a stirring rate of 200 rpm and an initial pH value of 7, the testing bacterial strain was cultured at a moderate temperature of 35° C. and a high temperature of 55° C.

B. Test for Different Bacterial Strains

According to a suitable culturing medium formula determined by the foregoing tests, a suitable culturing medium was prepared. After that, by using this suitable culturing medium, under a stirring rate of 200 rpm, an initial pH value of 7, and at 55° C., different testing bacterial strains were cultured.

2. Result 2.1 Tests for Known Culturing Medium

In the experiments of the present disclosure, the TSB medium used in bacterial strain selection and bacterial cell activation is a commercial medium. The TSB medium is suitable for culturing most microorganisms, does not have specificity, and the price thereof is higher.

In order to reduce the cost of culturing a bacterial strain and producing protein by a bacterial strain, this experiment used the above-mentioned literature medium to culture a test bacterial strain, *Tepidimonas fonticaldi* sp. nov. KCTC 12528BP. *Tepidimonas fonticaldi* sp. nov. KCTC 12528BP was deposited at the Korean Collection for Type Cultures (KCTC) on Dec. 4, 2013. The bacterium can be freely furnished. The *Tepidimonas fonticaldi* sp. nov. KCTC 12528BP is capable of secreting extracellular proteins.

Figure 1B:
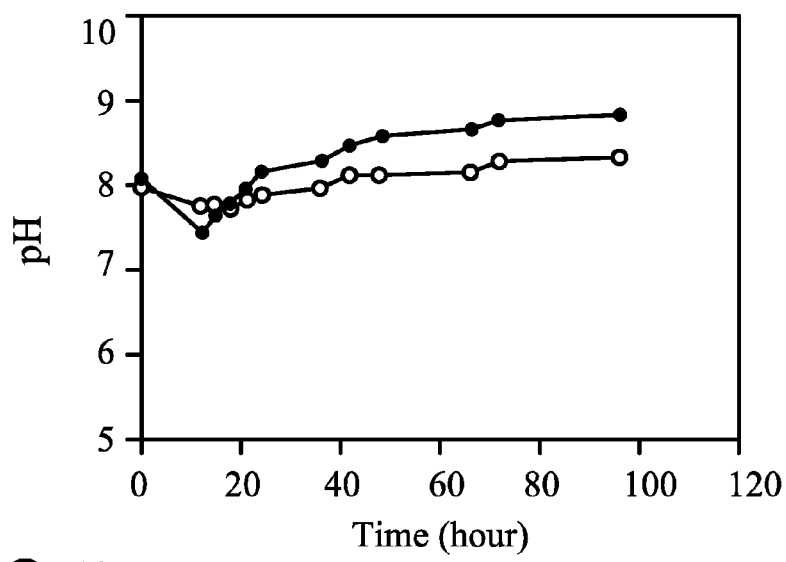
Figure 1C:
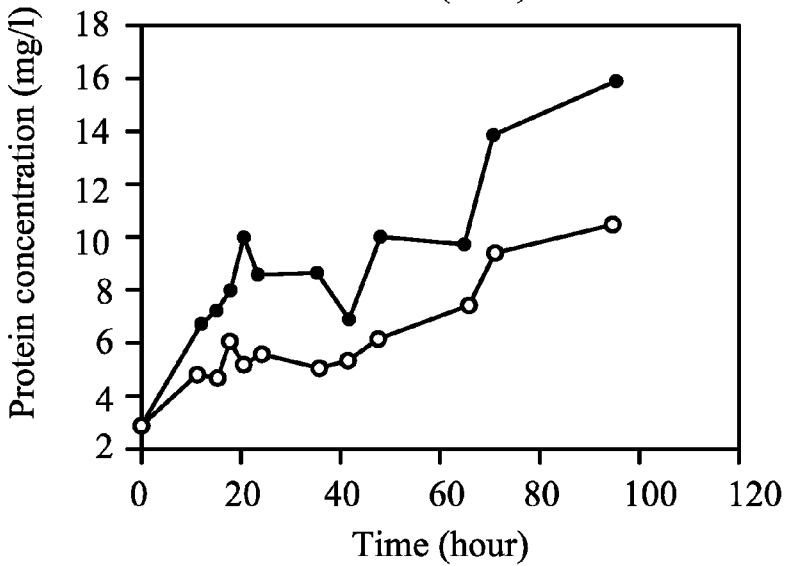

In this experiment, under an operational condition of 55° C., a stirring rate of 200 rpm and without controlling initial pH value, effects of 1/5-TSB medium or the literature medium on growth and protein production of *Tepidimonas fonticaldi* sp. nov. KCTC 12528BP were investigated. FIGS. 1A, 1B and 1C respectively shows the optical densities ($OD_{600}$), pH values, and protein concentration of the bacterial suspension were determined at different time points at a condition of culturing *Tepidimonas fonticaldi* sp. nov. KCTC 12528BP by the 1/5-TSB medium or the literature medium.

According to FIGS. 1A and 1C, it is clearly shown that *Tepidimonas fonticaldi* sp. nov. KCTC 12528BP is capable of growing in both the 1/5-TSB medium and the literature medium and secreting protein, and the bacterial cell concentration and protein concentration also rose as the culturing time increased.

Although when cultured *Tepidimonas fonticaldi* sp. nov. KCTC 12528BP by the literature medium, the resulting bacterial cell concentration and protein concentration was lower than those under culturing *Tepidimonas fonticaldi* sp. nov. KCTC 12528BP by the 1/5-TSB medium, most of the ingredients of the 1/5-TSB medium are complex ingredients, and in the opinion of researchers, that made it difficult to know the precise effective factors. In addition, the 1/5-TSB medium is a commercial medium and the prices thereof are high, and thus if the medium is applied in mass production for the bacterial strain, the commercial competitiveness will be decreased. Comparatively, the price of the literature medium is lower and literature medium has better research value.

Therefore, in the later experiments of the present disclosure, the literature medium was used as a base for a modified medium, and certain of the ingredients herein was added, deleted and/or replaced to form various modified mediums to determine suitable carbon sources, nitrogen sources, carbon source concentrations, nitrogen source concentrations and carbon-nitrogen ratio, to raise the bacterial cell concentration and protein yield of the bacterial strain in the culturing system.

2.2 Determination of Suitable Culturing Conditions

A. Test for Environmental Factors

*Tepidimonas fonticaldi* sp. nov. KCTC 12528BP is a thermophile bacterial strain, and the optimum growing temperature range for a thermophile bacterial strain is about 50-60° C., and the highest temperature does not exceed 90° C. Therefore, in this experiment, 1 mL of the activated bacterial strain was implanted into the literature medium to make the initial bacterial cell concentration about $OD_{600}$ 0.01-0.02, and after that under a stirring rate of 200 rpm and without controlling the initial pH value, the bacterial strain was cultured at temperatures of 50° C., 55° C., 60° C., 65° C. and 70° C., sampled at different time points, and the optical density ($OD_{600}$), protein concentration, and pH values of the bacterial suspension were analyzed.

Figure 2A:
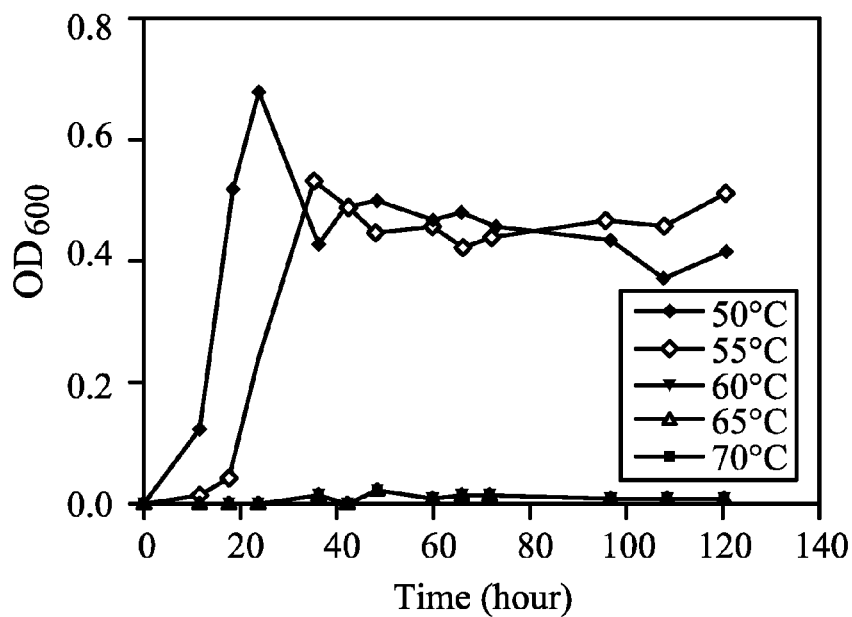
FIGS. 2A and 2B respectively show the optical densities ($OD_{600}$) of the bacterial suspension determined at different time points, and the effects of different culturing temperatures on *Tepidimonas fonticaldi* sp. nov. KCTC 12528BP secreting protein at a condition of culturing *Tepidimonas fonticaldi* sp. nov. KCTC 12528BP at different culturing temperatures.
Figure 2B:
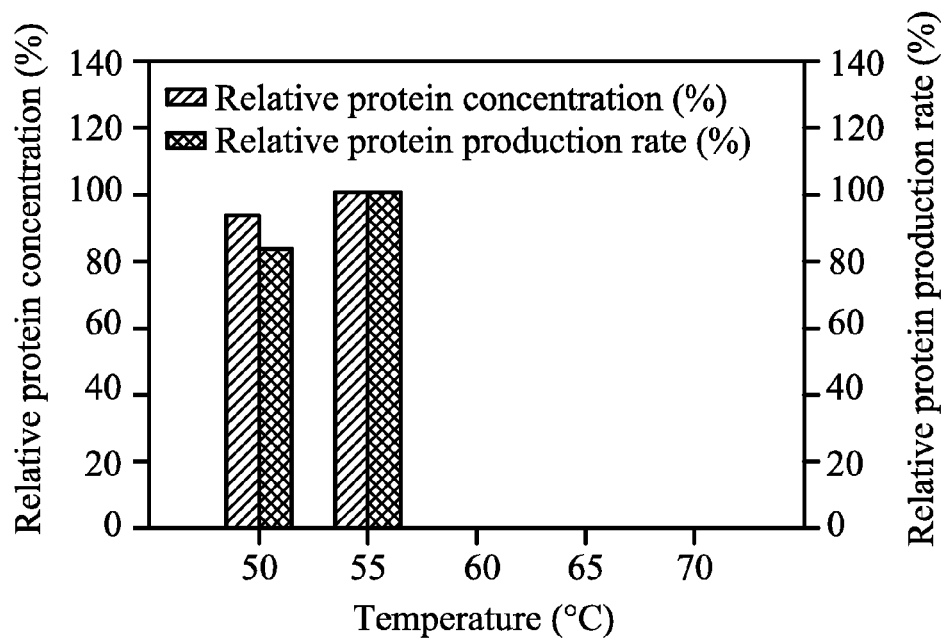

FIGS. 2A and 2B respectively show the optical densities ($OD_{600}$) of the bacterial suspension determined at different time points, and effects of different culturing temperatures on *Tepidimonas fonticaldi* sp. nov. KCTC 12528BP secreting protein at a condition of culturing *Tepidimonas fonticaldi* sp. nov. KCTC 12528BP at different culturing temperatures.

According to FIG. 2A and FIG. 2B, it is understood that under culturing temperatures of 50° C. and 55° C. are beneficial for the bacterial strain growth, and after the bacterial strain inoculation, the growth of the bacterial strain reaches an exponential/log phase in 24 hours. In the exponential/log phase, the metabolism of a bacterium is most vigorous and the number of the bacterium exponentially increases with time.

Furthermore, according to FIG. 2B, it is understood that under controlling the culturing temperature at 55° C., the concentration of the protein secreted by *Tepidimonas fonticaldi* sp. nov. KCTC 12528BP and protein production rate of *Tepidimonas fonticaldi* sp. nov. KCTC 12528BP are higher than those under culturing temperature at 50° C.

(2) Tests for Initial pH Value

After suitable culturing temperatures were determined, in this experiment, the bacterial strain was cultured at one of the suitable culturing temperatures, 55° C., and the effect of the initial culturing pH value on the bacterial strain was investigated. At an initial bacterial cell concentration of about $OD_{600}$ 0.01-0.02, a stirring rate of 200 rpm and a culturing temperature of 55° C., *Tepidimonas fonticaldi* sp. nov. KCTC 12528BP was cultured in the literature mediums with initial pH values of 5.0, 6.0, 7.0, 8.0 and 9.0.

Figure 3A:
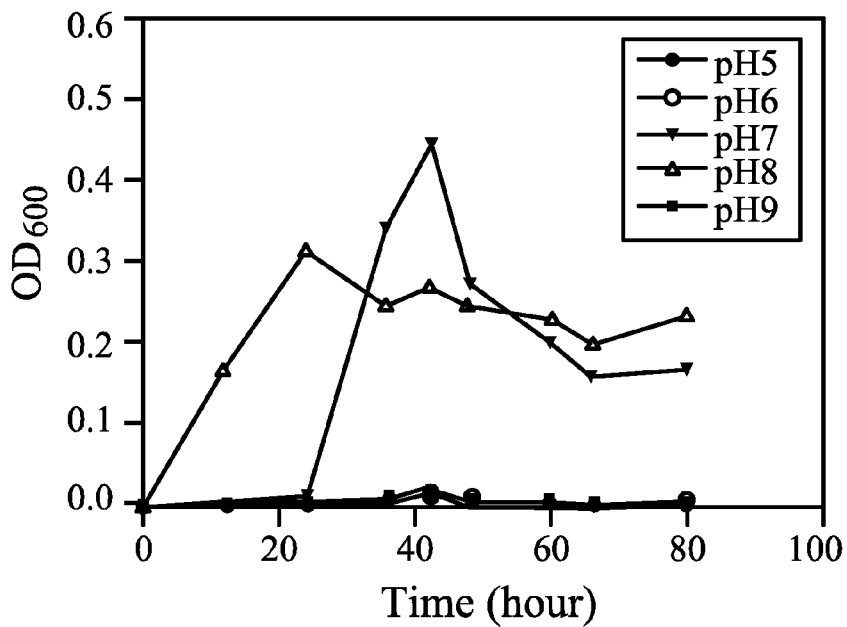
FIGS. 3A and 3B respectively show the optical densities ($OD_{600}$) of the bacterial suspension determined at different time points, and the effects of different initial culturing pH values on *Tepidimonas fonticaldi* sp. nov. KCTC 12528BP secreting protein at a condition of culturing *Tepidimonas fonticaldi* sp. nov. KCTC 12528BP at different initial culturing pH values.
Figure 3B:
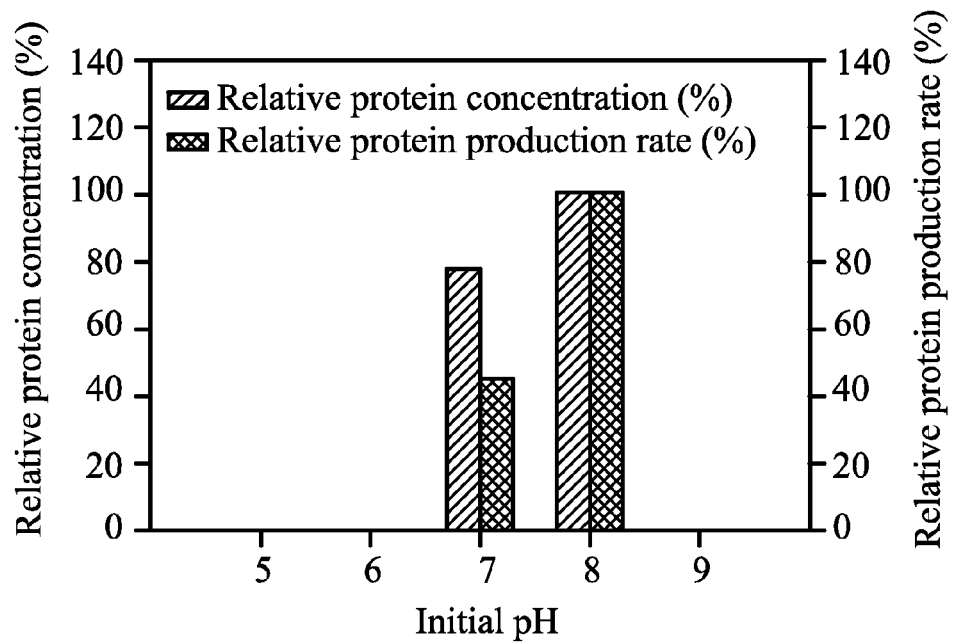

FIGS. 3A and 3B respectively show the optical densities ($OD_{600}$) of the bacterial suspension determined at different time points, and effects of different initial culturing pH values on *Tepidimonas fonticaldi* sp. nov. KCTC 12528BP secreting protein at a condition of culturing *Tepidimonas fonticaldi* sp. nov. KCTC 12528BP at different initial culturing pH values.

According to FIG. 3B, it is understood that an initial culturing pH value range of 7.0 to 8.0 is beneficial for bacterial strain growth. When the initial pH value of the culturing medium was controlled at pH 7.0, the lag phase of the growth of the bacterial strain was longer than that under controlling the initial pH value of the culturing medium at pH 8.0, and that showed that *Tepidimonas fonticaldi* sp. nov. KCTC 12528BP grew more easily in an environment of pH 8.0.

Furthermore, according to FIG. 3B and FIG. 3B, it is understood that under controlling the initial pH value at pH 8.0, the concentration of the protein secreted by *Tepidimonas fonticaldi* sp. nov. KCTC 12528BP and protein production rate of *Tepidimonas fonticaldi* sp. nov. KCTC 12528BP are higher than those under controlling the initial pH value at pH 7.0.

(3) Test for Stirring Rate

In this experiment, the bacterial strain was cultured at one of the suitable culturing temperatures, 55° C., and a suitable initial pH value of 8.0, and the effect of the a stirring rate on the bacterial strain was investigated. Under an initial bacterial cell concentration of about $OD_{600}$ 0.01-0.02, a culturing temperature of 55° C., and an initial pH value of 8.0, *Tepidimonas fonticaldi* sp. nov. KCTC 12528BP was cultured in the literature mediums with stirring rates of 0 rpm, 100 rpm or 200 rpm.

Figure 4A:
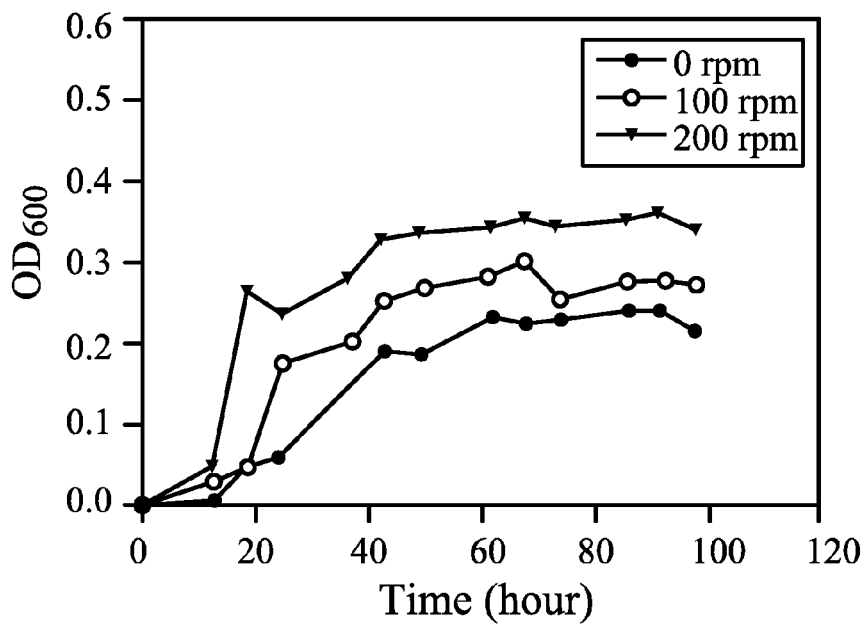
FIGS. 4A and 4B respectively show the optical densities ($OD_{600}$) of the bacterial suspension determined at different time points, and effects of different stirring rates on *Tepidimonas fonticaldi* sp. nov. KCTC 12528BP secreting protein at a condition of culturing *Tepidimonas fonticaldi* sp. nov. KCTC 12528BP at different stirring rates.
Figure 4B:
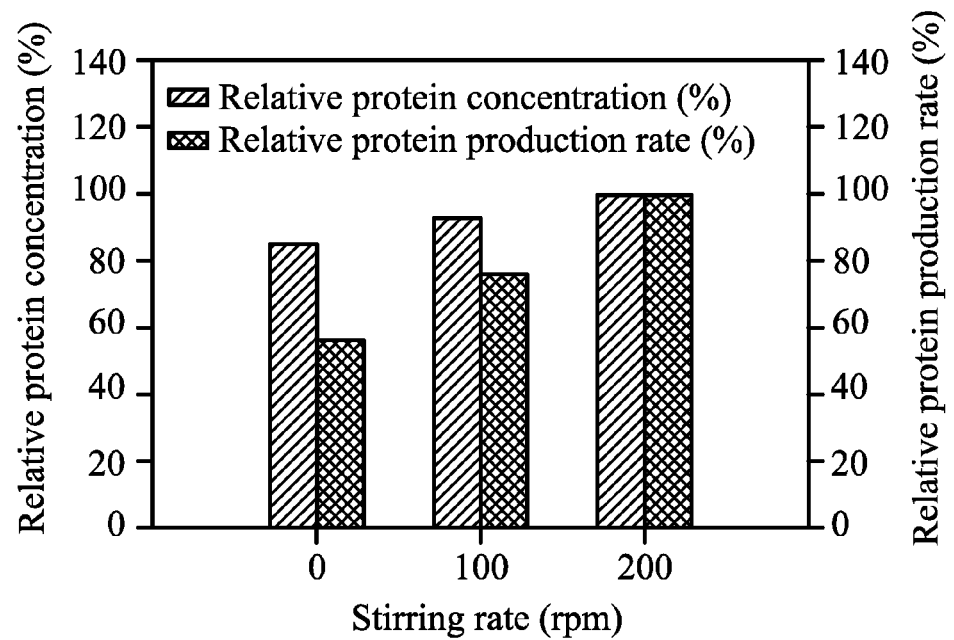

FIGS. 4A and 4B respectively show the optical densities ($OD_{600}$) of the bacterial suspension determined at different time points, and effects of different stirring rates on *Tepidimonas fonticaldi* sp. nov. KCTC 12528BP secreting protein at a condition of culturing *Tepidimonas fonticaldi* sp. nov. KCTC 12528BP at different stirring rates.

According to FIG. 4A, it is understood that the bacterial strain can grow under all kinds of stirring rates while the bacterial strain grow best with the stirring rate of 200 rpm.

Moreover, FIG. 4B shows that under controlling the stirring rate at 200 rpm, the concentration of the protein secreted by *Tepidimonas fonticaldi* sp. nov. KCTC 12528BP and protein production rate of *Tepidimonas fonticaldi* sp. nov. KCTC 12528BP were higher than those under controlling the stirring rate at 0 or 100 rpm.

B. Test for Composition of the Culturing Medium (1) Test for Carbon Sources

In this experiment, first, glucose of monosaccharide, sucrose of disaccharide, and starch of polysaccharide were used as carbon sources to investigate the effects of different carbohydrate carbon sources on *Tepidimonas fonticaldi* sp. nov. KCTC 12528BP secreting protein.

The literature medium was used as a base for a modified medium, and glucose, sucrose or starch was added to the literature medium to respectively form different modified mediums containing different carbon sources, and the amounts of glucose, sucrose and starch are added based on the amount of dextrose in the 1/5 TBS medium (Table 1) to be 0.5 g/L. After that, the testing bacterial strain was cultured by the different modified mediums containing different carbon sources.

Figure 5A:
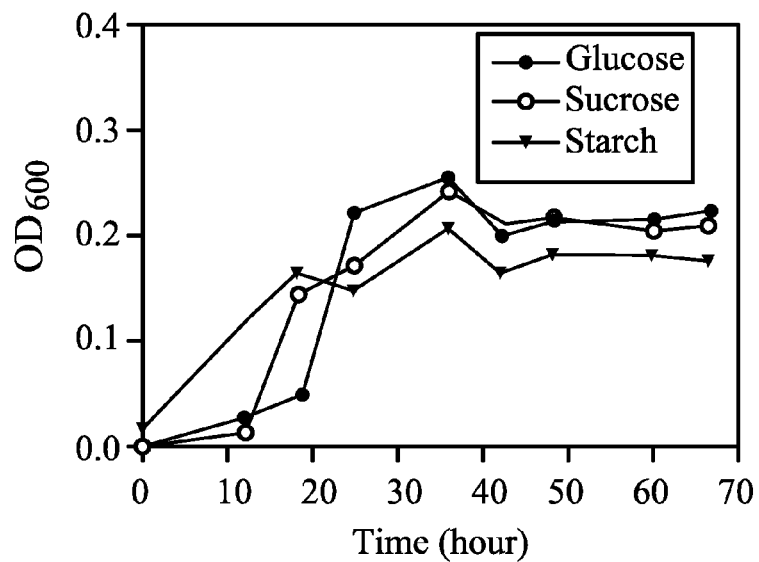
FIGS. 5A, 5B and 5C respectively show the optical densities ($OD_{600}$), pH values, and protein concentrations of the bacterial suspension determined at different time points at a condition of culturing *Tepidimonas fonticaldi* sp. nov. KCTC 12528BP with different carbon sources.
Figure 5B:
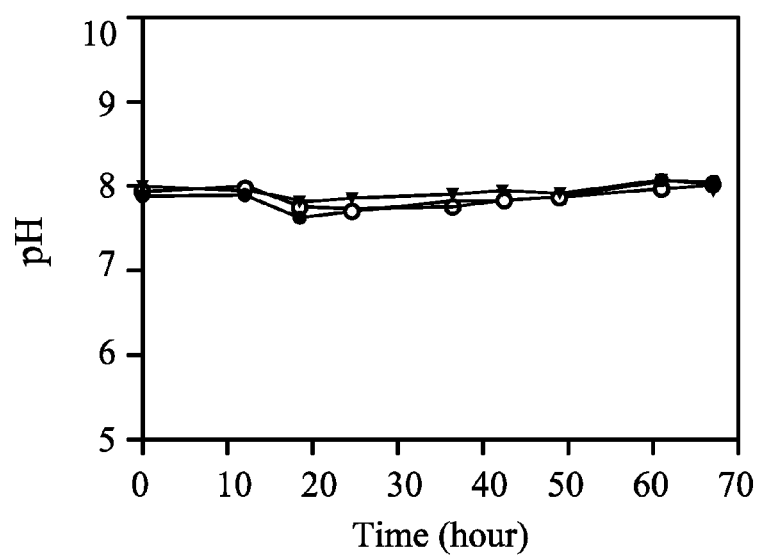
Figure 5C:
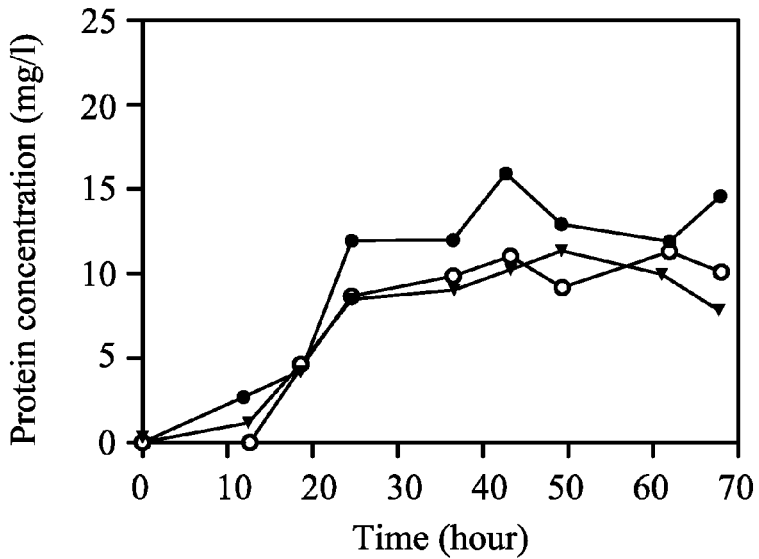

The testing results for different carbon sources as shown in FIGS. 5A, 5B and 5C. FIGS. 5A, 5B and 5C respectively show the optical densities ($OD_{600}$), pH values, and protein concentrations of the bacterial suspension determined at different time points at a condition of culturing *Tepidimonas fonticaldi* sp. nov. KCTC 12528BP with different carbon sources.

According to FIG. 5A, it is understood that when different carbohydrates were used as different carbon sources, there was no significant difference for the growth of the bacterial strain, and the concentrations of the protein produced by the bacterial strain are not high, only reached to about 10 mg/L (see FIG. 5C).

In order to find out a carbon source which effectively support the growth of the bacterial strain and enable the bacterial strain to secrete protein, this experiment further used acetate, lactate or butyrate of organic acid as a carbon source besides glucose. The amount of acetate, lactate or butyrate was added 0.5 g/L, identically. In the course of the experiment, in addition to periodically sampling the bacterial suspensions in different carbon source environments and determining the optical densities ($OD_{600}$) and protein concentrations thereof, the variation of the carbon source concentration in the testing system was further analyzed by high-performance liquid chromatography to realize the carbon source utilization for the bacterial strain. The results are shown as FIGS. 6A, 6B and 6C.

Figure 6A:
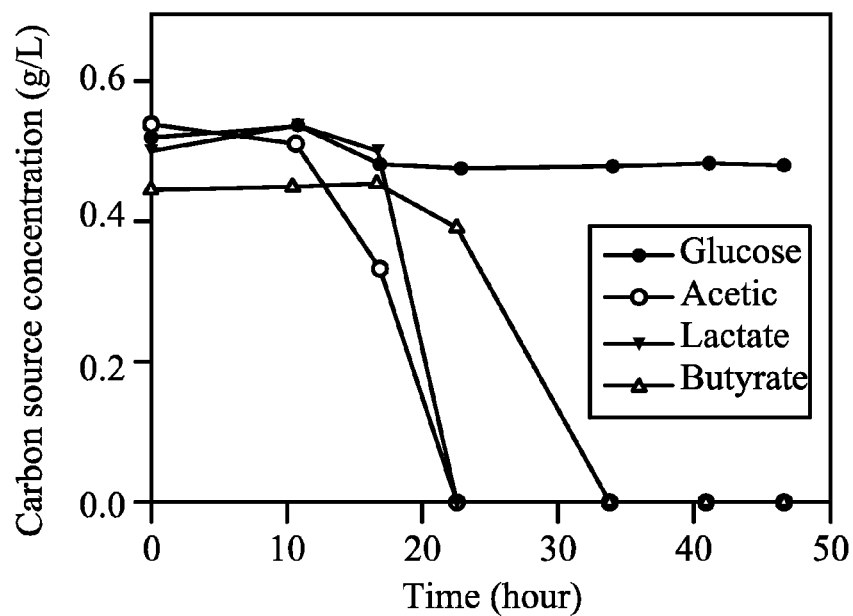
FIG. 6A and FIG. 6B respectively show the carbon source concentrations and the optical densities ($OD_{600}$) of the bacterial suspension determined at different time points at a condition of culturing *Tepidimonas fonticaldi* sp. nov. KCTC 12528BP with a carbohydrate or organic acids.
Figure 6B:
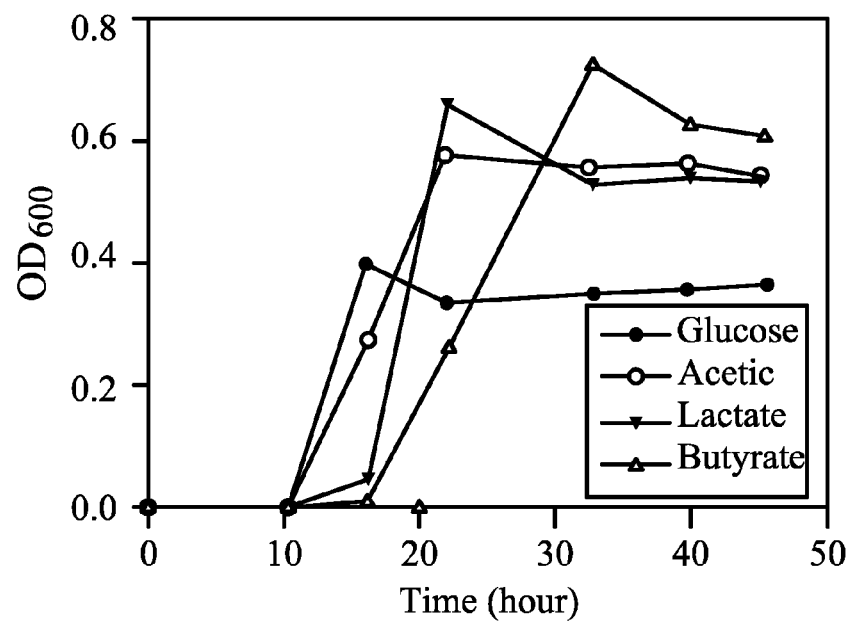
Figure 6C:
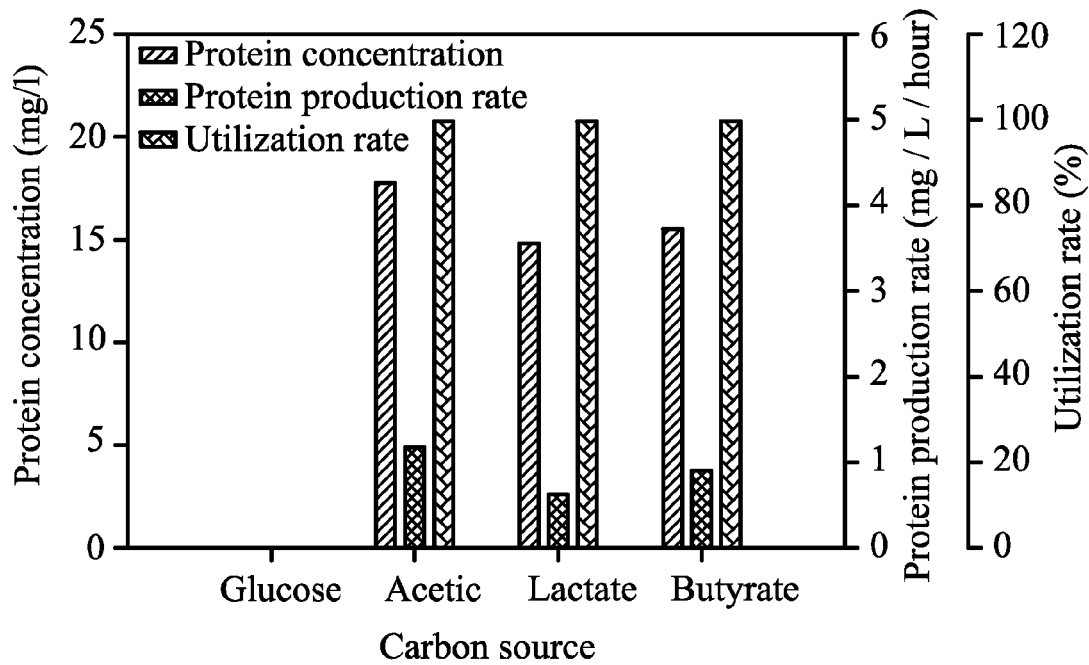
FIG. 6C shows the effects of different carbon sources on *Tepidimonas fonticaldi* sp. nov. KCTC 12528BP secreting protein.

FIG. 6A and FIG. 6B respectively show the carbon source concentrations and the optical densities ($OD_{600}$) of the bacterial suspension determined at different time points, and FIG. 6C shows the effects of different carbon sources on *Tepidimonas fonticaldi* sp. nov. KCTC 12528BP secreting protein at a condition of culturing *Tepidimonas fonticaldi* sp. nov. KCTC 12528BP with a carbohydrate or an organic acid.

According to FIG. 6A, it is known that *Tepidimonas fonticaldi* sp. nov. KCTC 12528BP hardly utilized simple carbohydrate carbon source (glucose), and when glucose was used as the carbon source, the growth of the bacterial cell was slower, and the highest optical density ($OD_{600}$) of the bacterial suspension is only about 0.4 (FIG. 6B); however, when an organic acid (acetate, lactate or butyrate) was used as the carbon source, the bacterial strain could completely consume the acetate and the lactate in a reaction time of about 22 hours while completely decompose the butyrate in a reaction time of about 33 hours. In the environment of organic acid, the optical density ($OD_{600}$) of the bacterial suspension could reach about 0.6-0.7, which is 1.5-1.9 times that in the environment of carbohydrate carbon source.

FIG. 6B shows that by using butyrate as the carbon source, the optical density ($OD_{600}$) of *Tepidimonas fonticaldi* sp. nov. KCTC 12528BP reached about 0.7, which was the highest among those of all test carbon sources, and the next was by using lactate and by using acetate, sequentially; however, in the light of growth rate of exponential/log phase of the bacterial strain, the growth rates in the three organic acids are: lactate>acetate>butyrate. Moreover, in light of bacterial strain growth in the lag phase, the lag phase by using acetate as the carbon source was significantly shorter than that by using lactate or butyrate as the carbon source. In light of the protein production rate, using acetate as the carbon source was the best, after which came lactate, and the protein production rates for acetate and lactate were 1.2 mg/L and 0.94 mg/mL per hour, respectively.

In summary, under a fixed growth condition of a temperature of 55° C., a stirring rate of 200 rpm, an initial pH value of 8.0, and an initial bacterial cell concentration of about $OD_{600}$ 0.01-0.02, by using acetate as the carbon source, *Tepidimonas fonticaldi* sp. nov. KCTC 12528BP could have the highest growth concentration and highest protein concentration and protein production rate, and thus acetate was selected as the target carbon source to carry out the subsequent estimation of nitrogen source.

(2) Test for Nitrogen Sources

In this experiment, ammonium sulfate (($NH_4$)$_2SO_4$), ammonium nitrate ($NH_4NO_3$), ammonium chloride ($NH_4Cl$) and urea were used as nitrogen sources to investigate the effects of different nitrogen sources on *Tepidimonas fonticaldi* sp. nov. KCTC 12528BP secreting protein.

Figure 7:
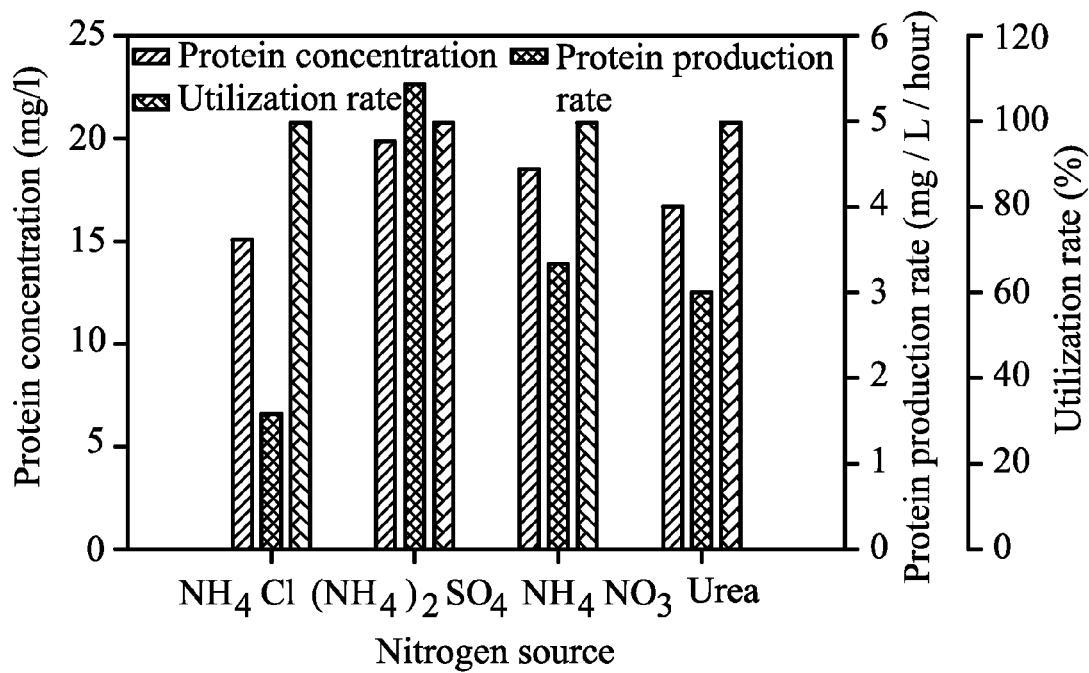
FIG. 7 shows the effects of different nitrogen sources on *Tepidimonas fonticaldi* sp. nov. KCTC 12528BP secreting protein.

The literature medium was used as a base for a modified medium, and under a fixed growth condition of using acetate as the carbon source, a temperature of 55° C., a stirring rate of 200 rpm, an initial pH value of 8.0, and an initial bacterial cell concentration of about $OD_{600}$ 0.01-0.02, ammonium sulfate (($NH_4$)$_2SO_4$), ammonium nitrate ($NH_4NO_3$), ammonium chloride ($NH_4Cl$) or urea was used as the nitrogen sources to culture *Tepidimonas fonticaldi* sp. nov. KCTC 12528BP, and the contents for the four different nitrogen sources in the culturing mediums were $NH_4Cl$ 0.30 g/L, ($NH_4$)$_2SO_4$ 0.74 g/L, $NH_4NO_3$ 0.22 g/L and urea 0.17 g/L. The effects of different nitrogen sources on *Tepidimonas fonticaldi* sp. nov. KCTC 12528BP secreting protein are shown in FIG. 7.

The four kinds of nitrogen source all could substantially raise the protein production rate and protein concentration of *Tepidimonas fonticaldi* sp. nov. KCTC 12528BP, and the effect of raising the protein production rate is especially significant. FIG. 7 shows that, among the four different nitrogen sources, ammonium sulfate has the best effect of raising protein production rate, wherein the highest protein production rate is raised from 1.2 mg/L/hr under no addition to about 5.4 mg/L/hr. Therefore, in the subsequent experiments, acetate was used as the carbon source and ammonium sulfate was used as the nitrogen source to carry out the investigation of the optimum concentration of the carbon source and the nitrogen source of the culturing medium.

(3) Test for Carbon Source Concentrations

In this experiment, under a fixed nitrogen source concentration (ammonium sulfate, 0.74 g/L), the effect of changing the concentration of the carbon source (acetate) on *Tepidimonas fonticaldi* sp. nov. KCTC 12528BP secreting protein was investigated.

The literature medium was used as a base for a modified medium, and under a fixed growth condition of using ammonium sulfate as the nitrogen source (0.74 g/L), a temperature of 55° C., a stirring rate of 200 rpm, an initial pH value of 8.0, and an initial bacterial cell concentration of about $OD_{600}$ 0.01-0.02, the culturing mediums with carbon source concentrations of 0.5 g/L, 1.0 g/L 2.0 g/L, 3.0 g/L, 4.0 g/L and 5.0 g/L were prepared to culture *Tepidimonas fonticaldi* sp. nov. KCTC 12528BP.

The manner of estimating the optimum concentration for the carbon source uses the specific growth rate ($\mu$) of the microorganism as the reference. The specific growth rate means the bacterial cell amount increased by one unit mass of the bacterial cell per hour, and is a parameter for growth rate of a microorganism.

According to the optical densities ($OD_{600}$) of the bacterial suspensions cultured under different carbon source concentrations determined with time, it is known that under carbon source concentrations of 0.5 g/L, 1.0 g/L, 2.0 g/L, 3.0 g/L, 4.0 g/L and 5.0 g/L, the final optical densities ($OD_{600}$) of the bacterial suspensions were 0.539, 0.562, 1.012, 1.300, 1.302 and 0.314, respectively; while the specific growth rates for the respective carbon source concentrations obtained by the regression result from the log bacterial concentration-time diagram were 0.140, 0.170, 0.525, 0.527, 0.190 and 0.115 $hr^{-1}$ (see Table 3).

TABLE 3

The specific growth rates of the bacterial strain under different carbon source concentrations

| Addition concentration for carbon source (g/L) | Specific growth rate ($\mu$) ($hr^{-1}$) | $R^2$ |
|---|---|---|
| 0.5 | 0.140 | 0.683 |
| 1.0 | 0.170 | 0.919 |
| 2.0 | 0.525 | 0.999 |
| 3.0 | 0.527 | 0.999 |
| 4.0 | 0.190 | 0.774 |
| 5.0 | 0.115 | 0.831 |

According to the data shown above, for specific growth rates, when the concentration of acetate were 2.0 g/L and 3.0 g/L, the specific growth rates of the bacteria strain for these two concentrations were very close to each other, and higher than those for other concentrations. Considering the economical cost, in order to reduce the production cost of the bacterial strain, 2.0 g/L could be considered as an optimum concentration for the carbon source. Therefore, the subsequent investigation for the nitrogen source proceeded using this carbon source concentration.

(4) Test for Nitrogen Source Concentrations

In this experiment, under a fixed carbon source concentration (acetate, 2.0 g/L), the effect of changing the concentration of the nitrogen source (ammonium sulfate) on *Tepidimonas fonticaldi* sp. nov. KCTC 12528BP secreting protein was investigated.

The literature medium was used as a base for a modified medium, and under a fixed growth condition of using ammonium sulfate as the carbon source (2.0 g/L), a temperature of 55° C., a stirring rate of 200 rpm, an initial pH value of 8.0, and an initial bacterial cell concentration of about $OD_{600}$ 0.01-0.02, the culturing mediums with nitrogen source (ammonium sulfate) concentrations of 0.74 g/L, 1.0 g/L, 2.0 g/L, 3.0 g/L, 4.0 g/L and 5.0 g/L were prepared to culture *Tepidimonas fonticaldi* sp. nov. KCTC 12528BP, wherein the culturing time was 84 hours.

Figure 8A:
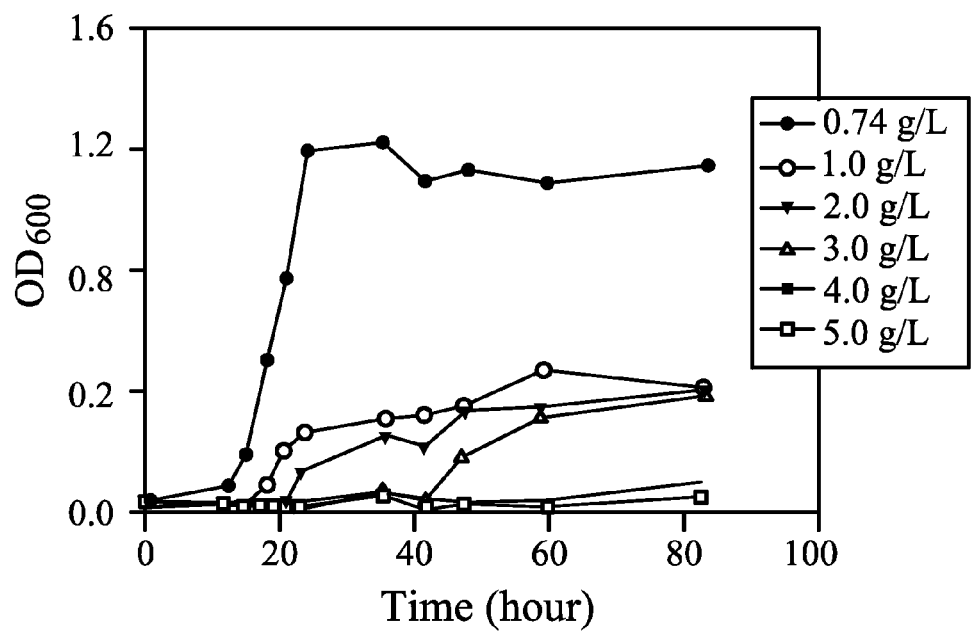
FIG. 8A and FIG. 8B respectively show the optical densities ($OD_{600}$) and protein concentrations of *Tepidimonas fonticaldi* sp. nov. KCTC 12528BP determined at different time points. Concentration of the carbon source is fixed at 2.0 g/L at different nitrogen source concentrations.

According to the results of the experiment, it was found that the concentration of the nitrogen source influences the growth of the bacterial strain. When the nitrogen source concentration was equal to or greater than 4.0 g/L, the excessive nitrogen source concentration in the system would inhibit the growth of the bacterial strain. When a small amount (0.74 g/L) of the nitrogen source was added to the system, the optical density ($OD_{600}$) of the bacterial cells was the highest among those for all other testing concentrations (see Table 4 and FIG. 8A).

Figure 8B:
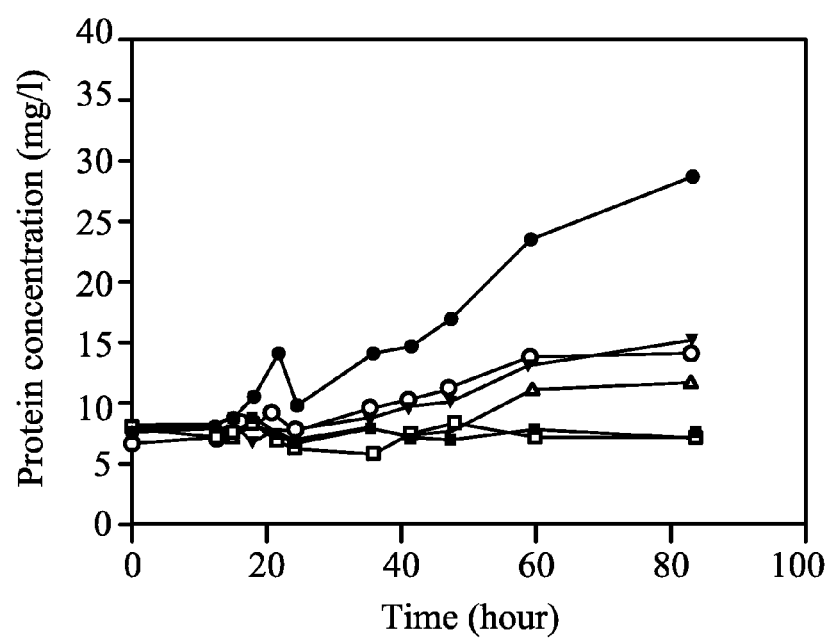

Furthermore, under different nitrogen source concentrations, the concentration of the protein produced in the system can be referred to in Table 4 and FIG. 8. Considering the addition amount of 0.74 g/L for the ammonium sulfate, the concentration of the protein produced in the system is about 30 mg/L, and is raised about 1.5-fold as compared with the concentration of 20 mg/L the protein produced in the system before the carbon and nitrogen source concentration tests (please refer to the protein concentration to ammonium sulfate shown in FIG. 7). Therefore, the subsequent investigation for the carbon-nitrogen ratio proceeded by 2.0 g/L of carbon source concentration and 0.74 g/L of nitrogen source concentration.

TABLE 4

The optical densities ($OD_{600}$) and protein concentrations of the bacterial strain

| Addition concentration for nitrogen source (g/L) | Optical density ($OD_{600}$) | Protein concentration (mg/L) |
|---|---|---|
| 0.74 | 1.174 | 29.42 |
| 1.0 | 0.415 | 14.12 |
| 2.0 | 0.421 | 15.11 |
| 3.0 | 0.393 | 11.40 |
| 4.0 | 0.109 | 7.11 |
| 5.0 | 0.046 | 6.76 |

(5) Test for Carbon-Nitrogen Ratios

The experiment for the effects of different carbon-nitrogen ratios on *Tepidimonas fonticaldi* sp. nov. KCTC 12528BP secreting protein was divided into two stages. In the first stage, effects of different carbon-nitrogen ratios on *Tepidimonas fonticaldi* sp. nov. KCTC 12528BP secreting protein under a fixed carbon weight was investigated; in the second stage, effects of different carbon-nitrogen ratios on *Tepidimonas fonticaldi* sp. nov. KCTC 12528BP secreting protein under a fixed nitrogen weight was investigated. All tests proceeded under a culturing condition of a temperature of 55° C., a stirring rate of 200 rpm, an initial pH value of 8.0, and an initial bacterial cell concentration of about $OD_{600}$ 0.01-0.02, wherein the culturing time was 96 hours.

(i) Test for Fixing Carbon Weight

According to the results of the tests for the carbon source shown above, the concentration of acetate was fixed at 2.0 g/L and the concentration of the nitrogen source varied to form formals with different carbon-nitrogen (C/N) ratios. The details of the formals are shown in Table 5.

TABLE 5

Formals with different carbon-nitrogen ratios under fixing the carbon weight

| C/N ratio | Acetate concentration (g/L) | Ammonium sulfate (g/L) |
|---|---|---|
| 1.2 | 2 | 3.2 |
| 2.4 | 2 | 1.6 |
| 4.7 | 2 | 0.8 |
| 5.1 | 2 | 0.74 |
| 7.07 | 2 | 0.53 |
| 9.4 | 2 | 0.4 |

Figure 9A:
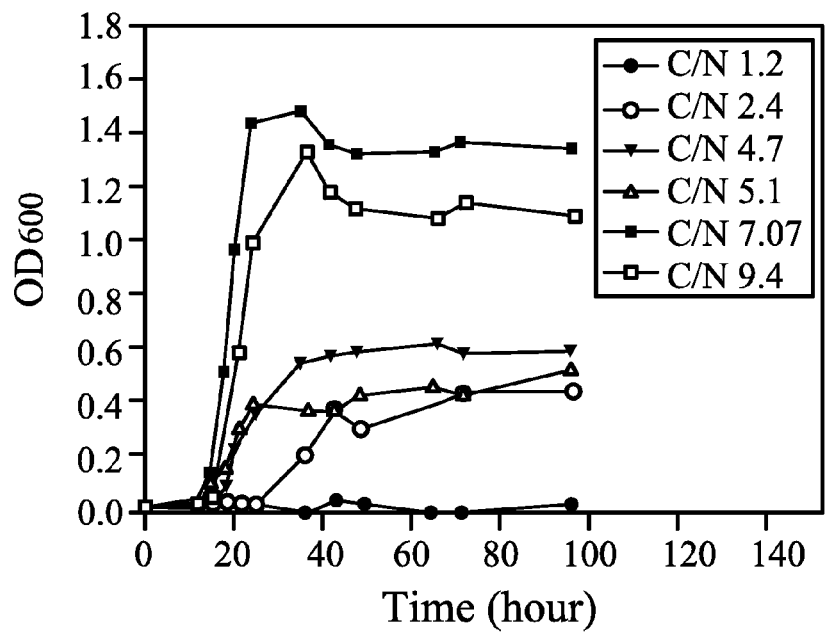
FIG. 9A and FIG. 9B respectively show the optical densities ($OD_{600}$) and protein concentrations of *Tepidimonas fonticaldi* sp. nov. KCTC 12528BP determined at different time points at fixed addition concentration for the carbon source of 2.0 g/L (carbon weight, 0.8 g) and different carbon-nitrogen ratios.

The results show that the excessive nitrogen source concentration in the system will inhibit the growth of the bacterial strain, and this phenomenon matches the results of tests for nitrogen source mentioned above. However, if the nitrogen concentration in the system is too low, that is also harmful to the growth of the bacterial strain. When the nitrogen source concentration was 0.4 g/L, the optical density of the bacterial strain was 1.144, and was lower than that for a nitrogen source concentration of 0.53 g/L, 1.396 (refer to Table 6 and FIG. 9A).

Figure 9B:
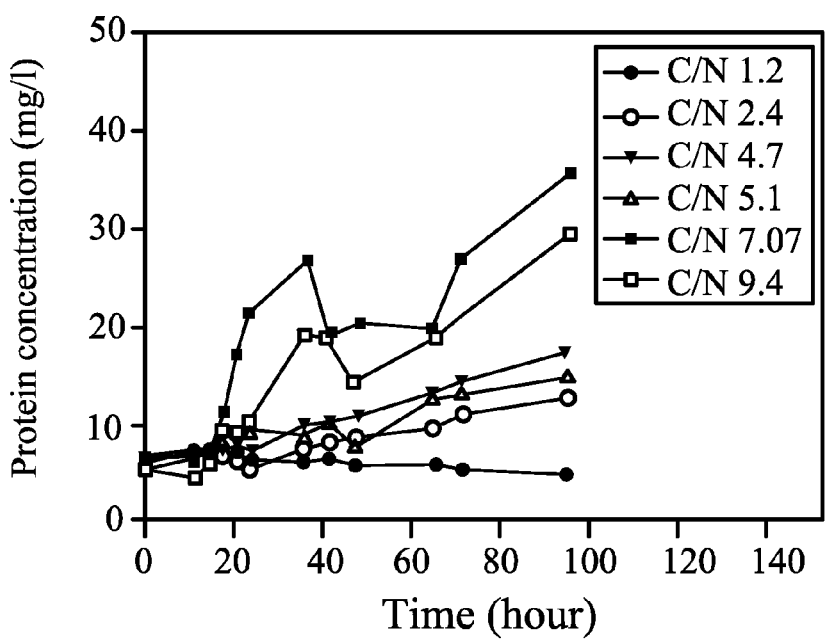

In addition, for the protein concentration, according to Table 6 and FIG. 9B, it is known that when the carbon-nitrogen ratio is 7.07, the protein concentration in the testing system reaches its highest (36.63 mg/L).

Therefore, according to the preceding results, it is known that, under a fixed carbon weight (acetate concentration, 2.0 g/L) and a carbon-nitrogen ratio of 7.07 (ammonium sulfate concentration, 0.53 g/L), the highest bacterial cell concentration and protein concentration can be obtained. Therefore, in the second stage of the test for carbon-nitrogen ratios, the test for fixing nitrogen carbon weight proceeded by fixing the ammonium sulfate concentration at 0.53 g/L and varying the carbon source concentration. After that, the results of the test for fixing carbon weight and the test for fixing nitrogen source were integrated and analyzed to find the most suitable carbon-nitrogen ratio for the growth of *Tepidimonas fonticaldi* sp. nov. KCTC 12528BP.

TABLE 6

The optical densities ($OD_{600}$) and protein concentrations of the bacterial strain under a fixed carbon weight and different carbon-nitrogen ratios

| C/N ratio | Optical density ($OD_{600}$) | Protein concentration (mg/L) |
|---|---|---|
| 1.2 | 0.016 | 5.04 |
| 2.4 | 0.468 | 12.98 |
| 4.7 | 0.607 | 17.72 |
| 5.1 | 0.544 | 15.16 |
| 7.07 | 1.396 | 36.63 |
| 9.4 | 1.144 | 29.82 |

(ii) Test for Fixing Nitrogen Weight

In this experiment, the ammonium sulfate concentration was fixed at 0.53 g/L based on the results for the test for carbon source, and the carbon source concentration was varied to form formals with different carbon-nitrogen (C/N) ratios. The details of the formals are shown in Table 7.

TABLE 7

Formals with different carbon-nitrogen ratios at a fixed nitrogen weight

| C/N ratio | Acetate concentration (g/L) | Ammonium sulfate (g/L) |
|---|---|---|
| 1 | 0.28 | 0.53 |
| 3 | 0.85 | 0.53 |
| 5 | 1.41 | 0.53 |
| 7.07 | 2 | 0.53 |
| 9 | 2.55 | 0.53 |
| 11 | 3.11 | 0.53 |
| 13 | 3.68 | 0.53 |
| 15 | 4.24 | 0.53 |

Figure 10A:
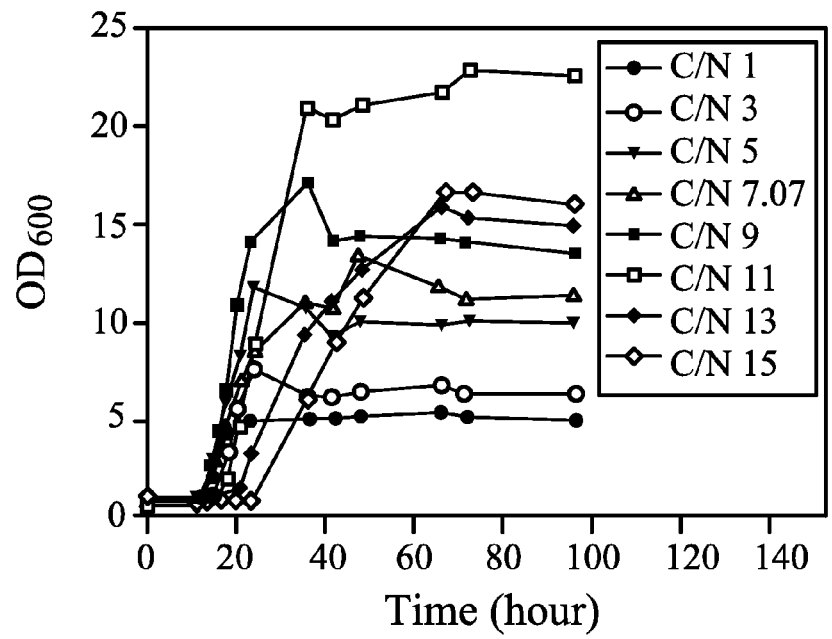
FIG. 10A and FIG. 10B respectively show the optical densities ($OD_{600}$) and protein concentrations of *Tepidimonas fonticaldi* sp. nov. KCTC 12528BP determined at different time points at a fixed addition concentration for the nitrogen source of 0.53 g/L (nitrogen weight, 0.11 g) and different carbon-nitrogen ratios.
Figure 10B:
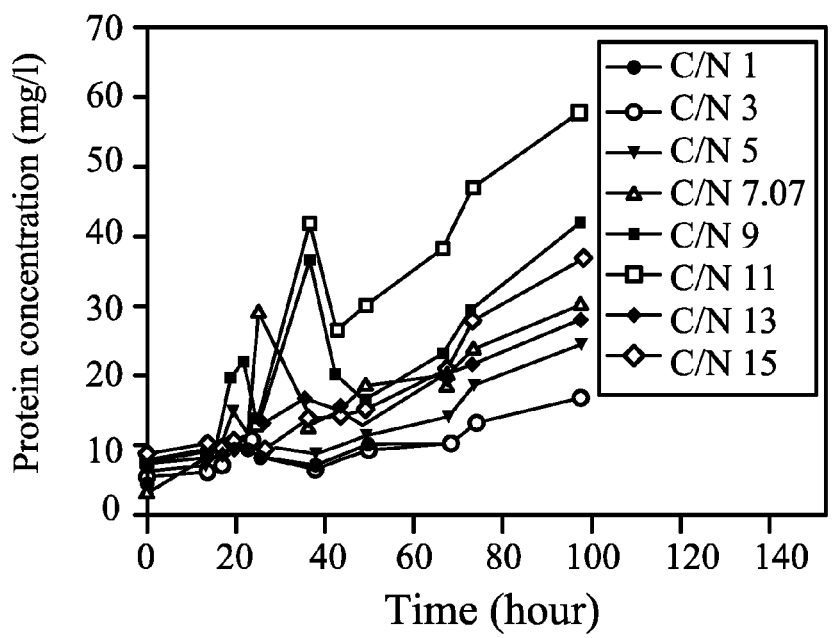

The results show that the optical densities ($OD_{600}$) of the bacterial cells will roughly increase as carbon source concentration increases, but when the addition concentration of the carbon source is higher than the optimum addition concentration, the excessive acetate will inhibit the growth of the bacterial strain in the system. Under a fixed nitrogen weight, the optical densities ($OD_{600}$) and protein concentrations of the bacterial strain in different experimental groups with different carbon-nitrogen ratios are shown in Table 8 and FIG. 10A. According to the experimental data, it is known that when the carbon-nitrogen ratio is 11, the optical density ($OD_{600}$) of the bacterial cells in the system reaches its highest. When the carbon-nitrogen ratio is 1 and when the carbon-nitrogen ratio is 15, the concentrations of bacterial cells in the system are on the low side. This shows that an excessively high or low carbon source concentration is harmful to the growth of the bacterial strain.

The estimation for the optimum carbon-nitrogen ratio under a fixed nitrogen weight proceeded in addition to by determining the bacterial cell concentration, also by determining the protein concentration in the system (Table 8 and 10B). Similarly, the protein concentration and the bacterial cell concentration in the system were in direct proportion, and the higher the bacterial cell concentration, the higher the concentration of the protein secreted by the bacterial cell. Therefore, in the second stage of the test for carbon-nitrogen ratios, under a fixed nitrogen weight (ammonium sulfate concentration, 0.53 g/L), a carbon-nitrogen ratio of 11 (acetate concentration, 3.11 g/L) was selected as the best carbon-nitrogen ratio.

TABLE 8

The optical densities ($OD_{600}$) and protein concentrations of the bacterial strain in different experimental groups with different carbon-nitrogen ratios

| C/N ratio | Optical density ($OD_{600}$) | Protein concentration (mg/L) |
|---|---|---|
| 1 | 0.497 | 16.88 |
| 3 | 0.643 | 17.18 |
| 5 | 1.008 | 25.47 |
| 7.07 | 1.152 | 30.61 |
| 9 | 1.360 | 43.44 |
| 11 | 2.292 | 58.65 |
| 13 | 1.500 | 29.03 |
| 15 | 1.628 | 37.52 |

(iii) Synthetic Evaluation

Figure 11:
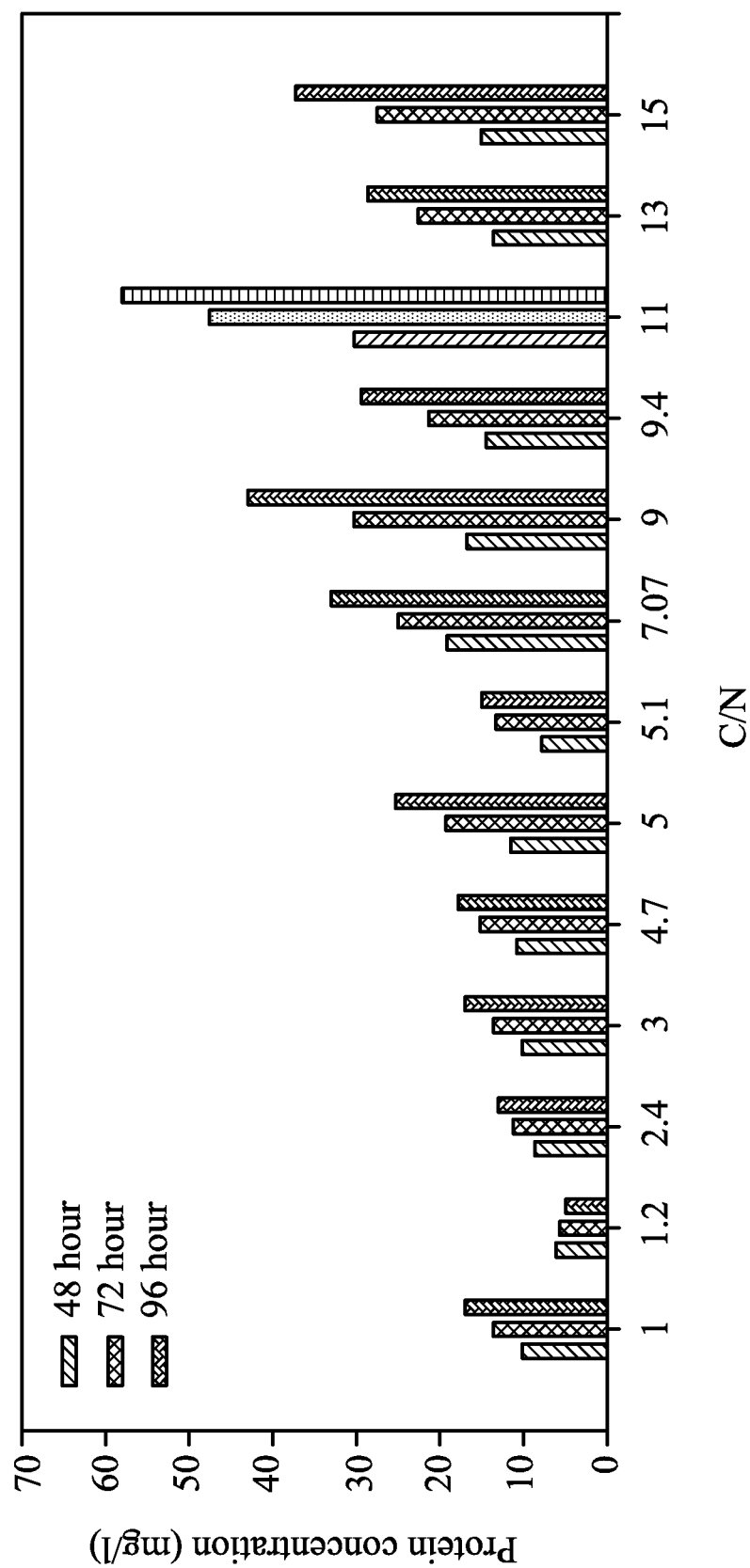
FIG. 11 shows at different carbon-nitrogen ratios, protein concentrations of *Tepidimonas fonticaldi* sp. nov. KCTC 12528BP determined at the 48 hour time point, the 72 hour time point and the 96 hour time point.

The analysis results of protein concentration at the 48-hour time point, the 72-hour time point and the 96-hour time point in the first stage (fixed carbon weight) and the second stage (fixed nitrogen weight) are integrated and shown in FIG. 11. According to FIG. 11, it is known that the protein concentration to a range of a carbon-nitrogen ratio from 7.07 to 15 is significantly better than that to the range of a carbon-nitrogen ratio from 1 to 5.1. Moreover, in the range of a carbon-nitrogen ratio from 7.07 to 15, the concentration of the protein produced by the bacterial strain under a carbon-nitrogen ratio of 11 was the best. Therefore, a carbon-nitrogen ratio of 11 was finally selected as the optimum carbon-nitrogen ratio for culturing *Tepidimonas fonticaldi* sp. nov. KCTC 12528BP.

According to the results of the various tests mentioned above, a novel culturing medium formula for culturing a bacterium of genus *Tepidimonas* was established in this experiment. The details of the formals are shown in Table 9.

TABLE 9

*Tepidimonas fonticaldi* sp. nov. KCTC 12528BP culturing medium established in the present disclosure

| Ingredients | Content (g/L) |
|---|---|
| Acetate | 3.11 |
| $Na_2HPO_4 \cdot 12H_2O$ | 5.30 |
| $KH_2PO_4$ | 1.50 |
| $(NH_4)_2SO_4$ | 0.53 |
| Yeast extract | 1.00 |
| $MgCl_2$ | 0.10 |
| Trace element solution | 1 mL/L |
| (Ingredients thereof are shown as below) | |
| Trace element solution | |
| $ZnSO_4 \cdot 7H_2O$ | 0.10 |
| $MnCl_2 \cdot 4H_2O$ | 0.03 |
| $H_3BO_3$ | 0.30 |
| $CoCl_2 \cdot 6H_2O$ | 0.20 |
| $CuCl_2 \cdot 2H_2O$ | 0.01 |
| $NiCl_2 \cdot 6H_2O$ | 0.02 |
| $Na_2MoO_4 \cdot 2H_2O$ | 0.03 |

Furthermore, under the same culturing condition, *Tepidimonas fonticaldi* sp. nov. KCTC 12528BP was cultured with the 1/5 TSB medium, the literature medium (Albuquerquea et al., 2006; Table 2) and the culturing medium of the present disclosure (Table 9), and the optical densities ($OD_{600}$) and protein concentrations of the bacterial suspension were determined.

Figure 12A:
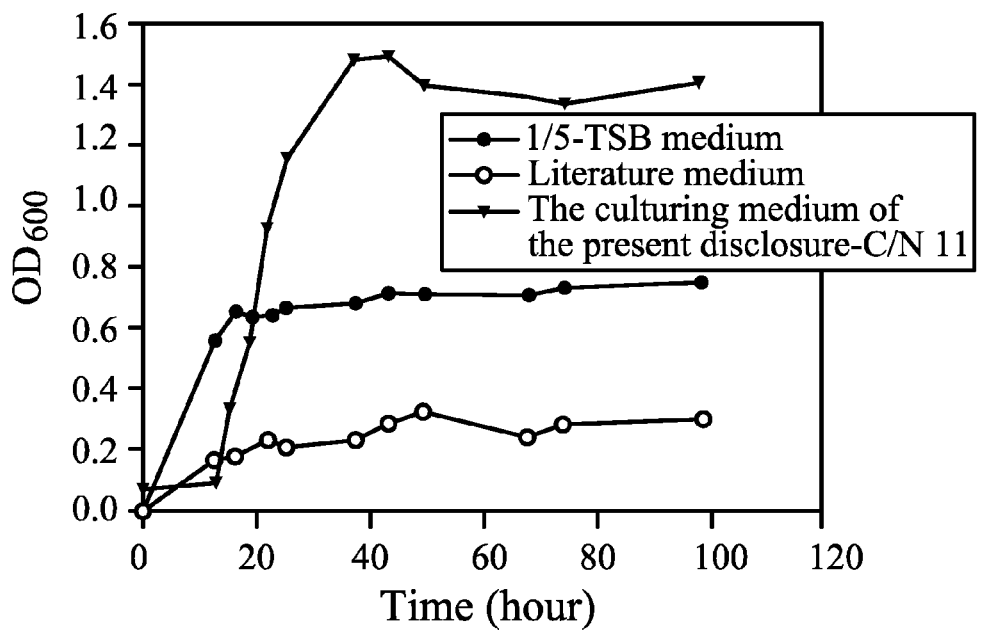
FIG. 12A and FIG. 12B respectively show the optical densities ($OD_{600}$) and protein concentrations of the bacterial suspension determined at different time points at a condition of culturing *Tepidimonas fonticaldi* sp. nov. KCTC 12528BP with the 1/5 TSB medium, the literature medium or the culturing medium of the present disclosure.
Figure 12B:
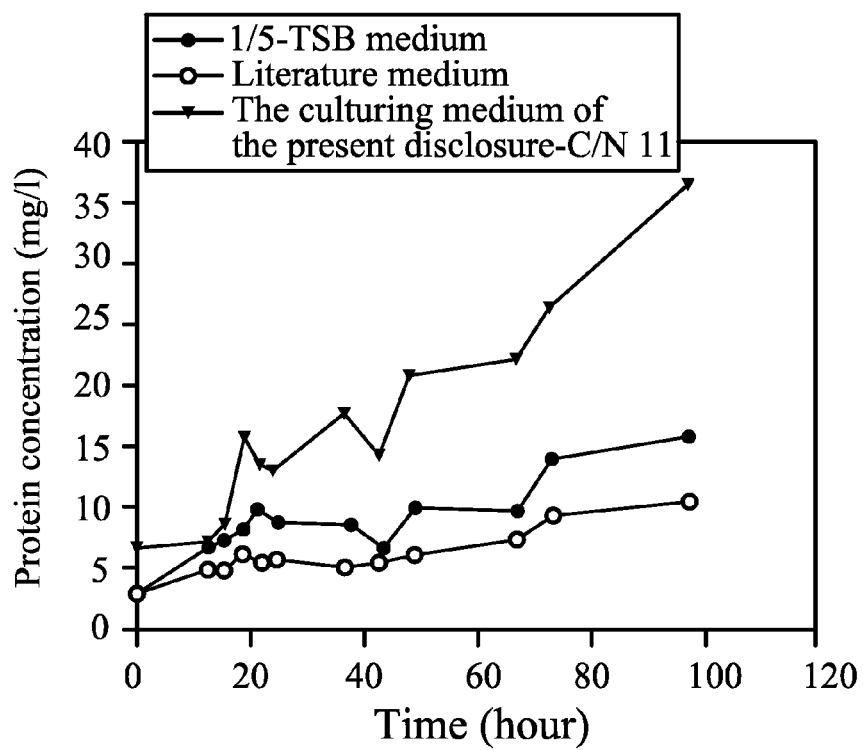

According to Table 10 and FIG. 12A and FIG. 12B, it is known that considering the growth of the bacterial cells or the protein concentration, the culturing medium of the present disclosure has better effects.

TABLE 10

Optical densities ($OD_{600}$) and protein concentrations of the bacterial suspension cultured by different mediums

| Medium | Optical density ($OD_{600}$) | Protein concentration (mg/L) |
|---|---|---|
| 1/5-TSB | 0.750 | 15.75 |
| Literature Medium | 0.301 | 10.47 |
| Medium of the present disclosure (C/N ratio: 11) | 1.400 | 36.33 |

(6) Test for Replacing $Na_2HPO_4 \cdot 12H_2O$ with $NaHCO_3$

In this experiment, bicarbonate ions which are abundantly present in the primary environment for the bacterial strain were used to replace hydrogen phosphate ions to determine whether the bicarbonate ions are more suitable to the growth of the bacterial strain and can reduce the culturing cost or not.

$NaHCO_3$ was used to replace $Na_2HPO_4 \cdot 12H_2O$ in the culturing medium of the present disclosure (Table 9) to investigate the effect of changing the composition of the culturing medium on the growth and protein production of *Tepidimonas fonticaldi* sp. nov. KCTC 12528BP. The replaced ingredients of the culturing medium are shown in Table 11.

TABLE 11

Culturing medium with replacement of $Na_2HPO_4 \cdot 12H_2O$ by $NaHCO_3$

| Ingredients | Content (g/L) |
|---|---|
| Acetate | 3.11 |
| $NaHCO_3$ | 2.49 |
| $KH_2PO_4$ | 1.50 |
| Yeast extract | 1 |
| $(NH_4)_2SO_4$ | 0.53 |
| $MgCl_2$ | 0.10 |
| Trace element solution | 1 mL/L |
| (Ingredients thereof are shown as below) | |
| Trace element solution | |
| $ZnSO_4 \cdot 7H_2O$ | 0.10 |
| $MnCl_2 \cdot 4H_2O$ | 0.03 |
| $H_3BO_3$ | 0.30 |
| $CoCl_2 \cdot 6H_2O$ | 0.20 |
| $CuCl_2 \cdot 2H_2O$ | 0.01 |
| $NiCl_2 \cdot 6H_2O$ | 0.02 |
| $Na_2MoO_4 \cdot 2H_2O$ | 0.03 |

All experiments proceeded in a culturing condition of a temperature of 55° C., a stirring rate of 200 rpm, and an initial bacterial cell concentration of about $OD_{600}$ 0.01-0.02 (the culturing medium containing $Na_2HPO_4$ had a pH value of 8.0; the culturing medium containing $NaHCO_3$ had a pH value of 7.0 or 8.0), wherein the culturing time was 96 hours.

Figure 13A:
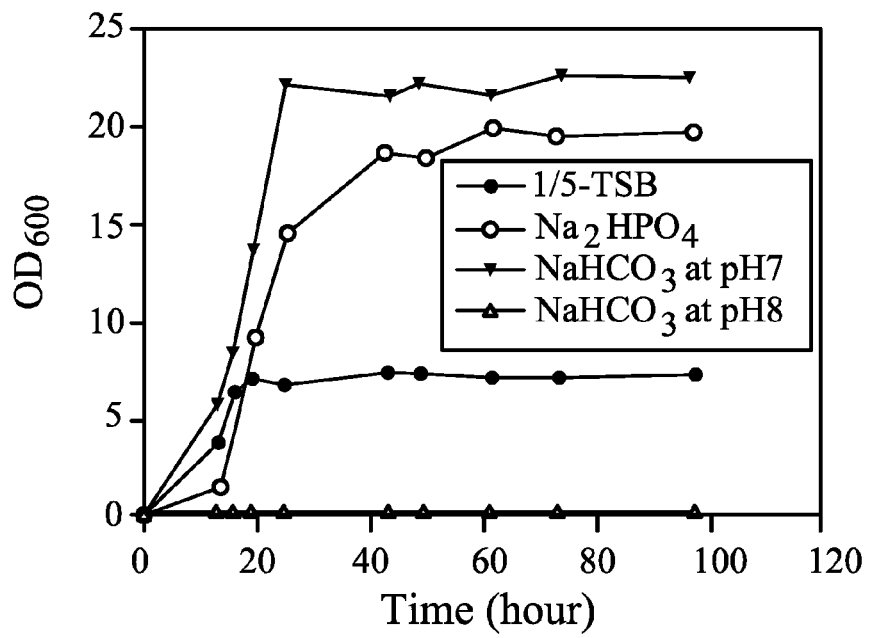
FIG. 13A and FIG. 13B respectively show the optical densities ($OD_{600}$) and protein concentrations of the bacterial suspension determined at different time points at a condition of culturing *Tepidimonas fonticaldi* sp. nov. KCTC 12528BP with the 1/5 TSB medium, the culturing medium of the present disclosure containing $Na_2HPO_4 \cdot 12H_2O$, and the culturing medium of the present disclosure containing $NaHCO_3$.
Figure 13B:
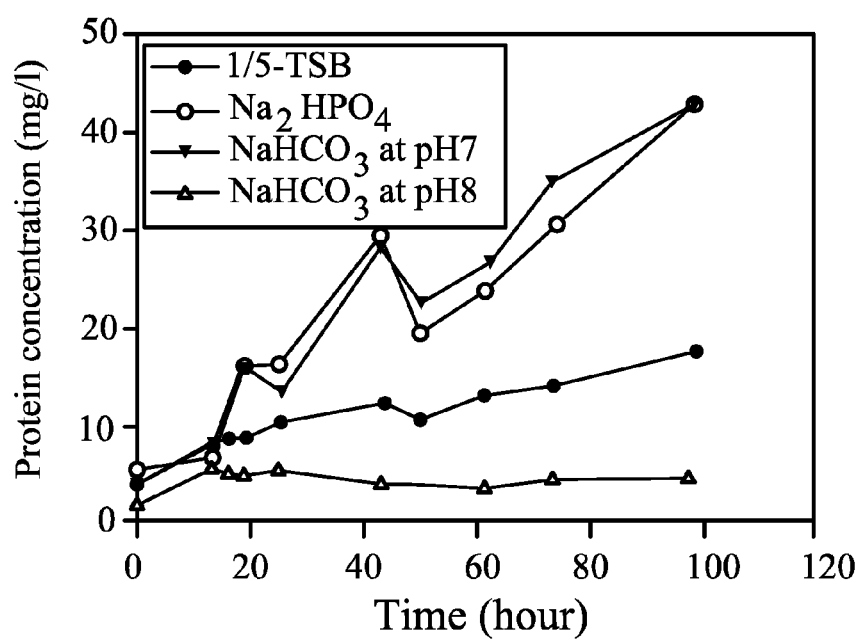

FIG. 13A and FIG. 13B respectively show the optical densities ($OD_{600}$) and protein concentrations of the bacterial suspension determined at different time points at a condition of culturing *Tepidimonas fonticaldi* sp. nov. KCTC 12528BP with the 1/5 TSB medium, the culturing medium of the present disclosure containing $Na_2HPO_4 \cdot 12H_2O$, and the culturing medium of the present disclosure containing $NaHCO_3$.

According to FIG. 13A and FIG. 13B, it is known that when *Tepidimonas fonticaldi* sp. nov. KCTC 12528BP is cultured under replacing $Na_2HPO_4 \cdot 12H_2O$ with $NaHCO_3$ and controlling the initial pH value at pH 7.0, the bacterial cell concentration and protein concentration in the system do not have significant difference from those of the bacterial strain cultured by the medium containing $Na_2HPO_4 \cdot 12H_2O$. Furthermore, using $NaHCO_3$ to replace $Na_2HPO_4 \cdot 12H_2O$ enabled the cost of the culturing medium dollars to be decreased from 21.22 NT to 7.83 NT dollars.

(7) Test for Yeast Extract

In this experiment, effects of the presence of the only complex ingredient, yeast extract, of the culturing medium of the present disclosure on the growth and protein production of *Tepidimonas fonticaldi* sp. nov. KCTC 12528BP were investigated.

The ingredients of the culturing medium, deleting the yeast extract therein, are shown in Table 12 (The ingredients of the culturing medium without deleting the yeast extract therein are shown in Table 11). All experiments proceeded in a culturing condition of a temperature of 55° C., a stirring rate of 200 rpm, an initial pH value of 7.0, and an initial bacterial cell concentration of about $OD_{600}$ 0.01-0.02, wherein the culturing time was 96 hours.

TABLE 12

Culturing medium without yeast extract

| Ingredients | Content (g/L) |
|---|---|
| Acetate | 3.11 |
| $NaHCO_3$ | 2.49 |
| $KH_2PO_4$ | 1.50 |
| $(NH_4)_2SO_4$ | 0.53 |
| $MgCl_2$ | 0.10 |
| Trace element solution (Ingredients thereof are shown as below) | 1 mL/L |
| Trace element solution | |
| $ZnSO_4 \cdot 7H_2O$ | 0.10 |
| $MnCl_2 \cdot 4H_2O$ | 0.03 |
| $H_3BO_3$ | 0.30 |
| $CoCl_2 \cdot 6H_2O$ | 0.20 |
| $CuCl_2 \cdot 2H_2O$ | 0.01 |
| $NiCl_2 \cdot 6H_2O$ | 0.02 |
| $Na_2MoO_4 \cdot 2H_2O$ | 0.03 |

Figure 14A:
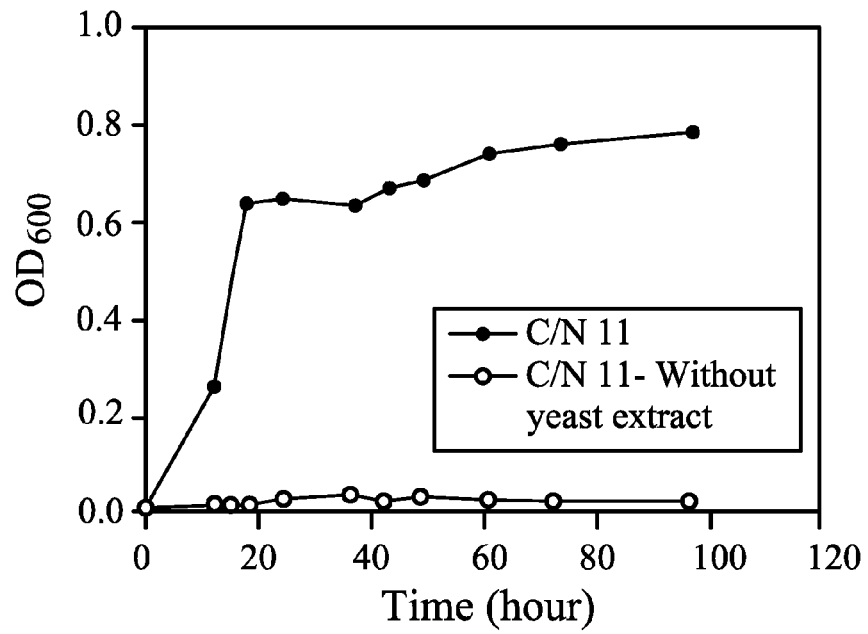
FIG. 14A and FIG. 14B respectively show the optical densities ($OD_{600}$) and protein concentrations of the bacterial suspension determined at different time points at a condition of culturing *Tepidimonas fonticaldi* sp. nov. KCTC 12528BP with the culturing medium of the present disclosure containing the yeast extract or the medium without yeast extract.
Figure 14B:
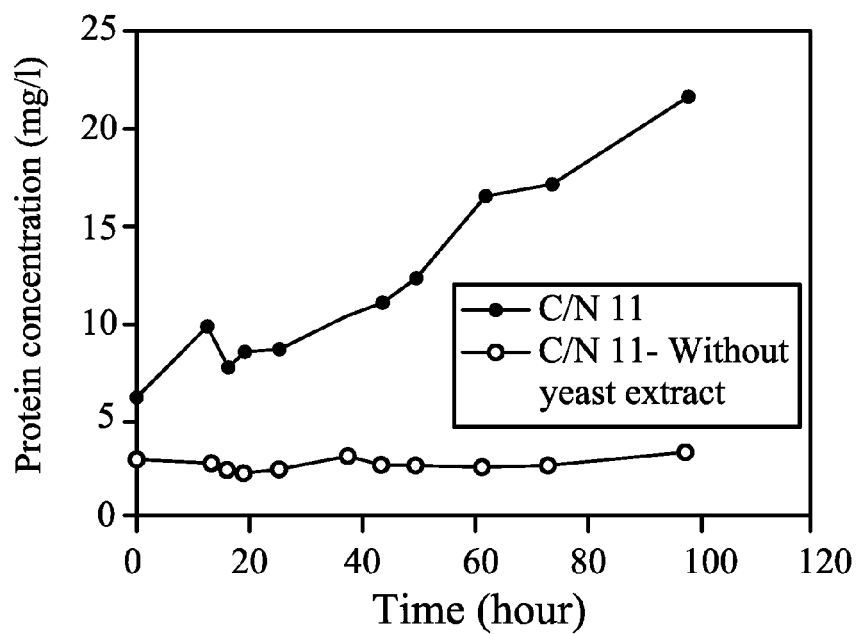

FIG. 14A and FIG. 14B respectively show the optical densities ($OD_{600}$) and protein concentrations of the bacterial suspension determined at different time points at a condition of culturing *Tepidimonas fonticaldi* sp. nov. KCTC 12528BP with the culturing medium of the present disclosure containing the yeast extract or the medium without yeast extract.

According to FIG. 14A and FIG. 14B, it is known that if the yeast extract is deleted, the bacterial strain cannot grow and produce protein.

2.3 Application Scope Tests for the Culturing Medium of the Present Disclosure

A. Test for Culturing Temperatures

In this experiment, effects of the medium of the present disclosure (Table 11) at a moderate temperature (35° C.) and at a high temperature (55° C.) on the growth and protein production of *Tepidimonas fonticaldi* sp. nov. KCTC 12528BP were investigated. All experiments proceeded in a culturing condition of a stirring rate of 200 rpm, an initial pH value of 7.0, and an initial bacterial cell concentration of about $OD_{600}$ 0.01-0.02, wherein the culturing time was 96 hours.

Figure 15A:
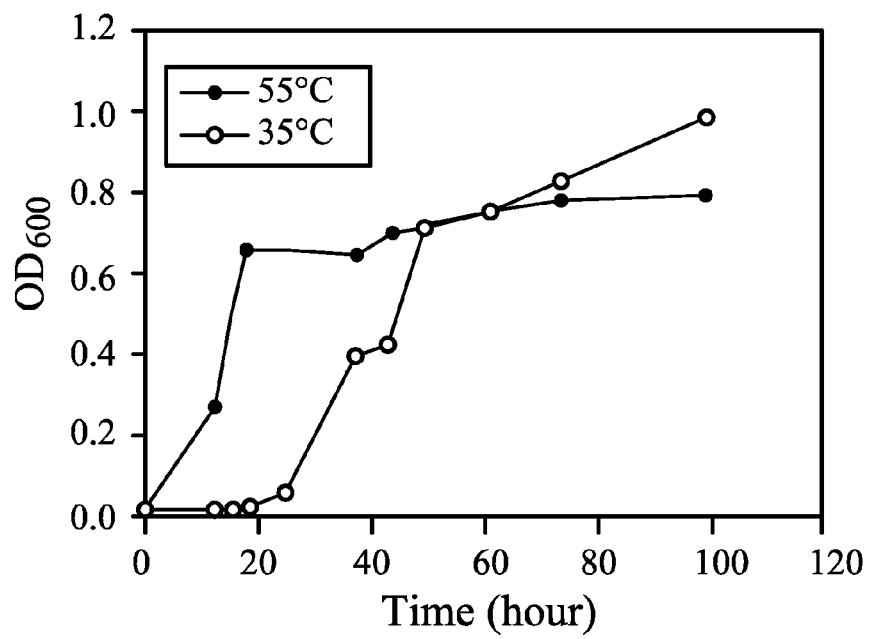
FIG. 15A and FIG. 15B respectively show the optical densities ($OD_{600}$) and protein concentrations of the bacterial suspension determined at different points in time at a condition of culturing *Tepidimonas fonticaldi* sp. nov. KCTC 12528BP with the culturing medium of the present disclosure at a moderate temperature (35° C.) and at a high temperature (55° C.)
Figure 15B:
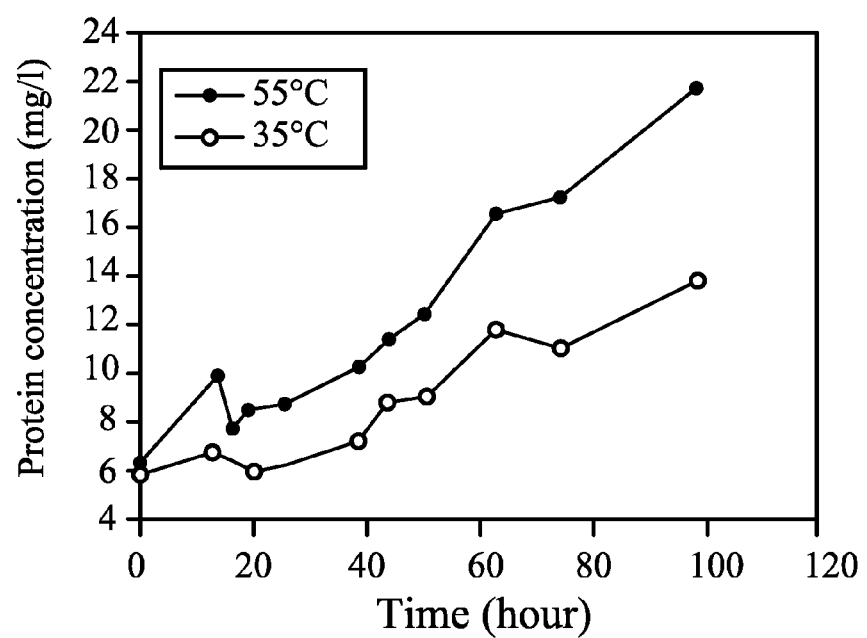

FIG. 15A and FIG. 15B respectively show the optical densities ($OD_{600}$) and protein concentrations of the bacterial suspension determined at different time points at a condition of culturing *Tepidimonas fonticaldi* sp. nov. KCTC 12528BP with the culturing medium of the present disclosure at a moderate temperature (35° C.) and at a high temperature (55° C.).

According to FIG. 15A and FIG. 15B, it is known that under culturing by the culturing medium of the present disclosure, no matter at a moderate temperature (35° C.) or at a high temperature (55° C.), the bacterial strain all can grow and produce protein, wherein the culturing medium of the present disclosure at the high temperature has better effects.

B. Culturing Test for Different Bacterial Strains

In this experiment, effects of the medium of the present disclosure (Table 11) on the growth and protein production of *Tepidimonas ignava* sps-1037 and *Tepidimonas aquatica*) CLN-1 which belong to the same genus to which *Tepidimonas fonticaldi* sp. nov. KCTC 12528BP belongs. All experiments proceeded in a culturing condition of a temperature of 55° C., a stirring rate of 200 rpm, an initial pH value of 7.0, and an initial bacterial cell concentration of about $OD_{600}$ 0.01-0.02, wherein the culturing time was 96 hours.

Figure 16A:
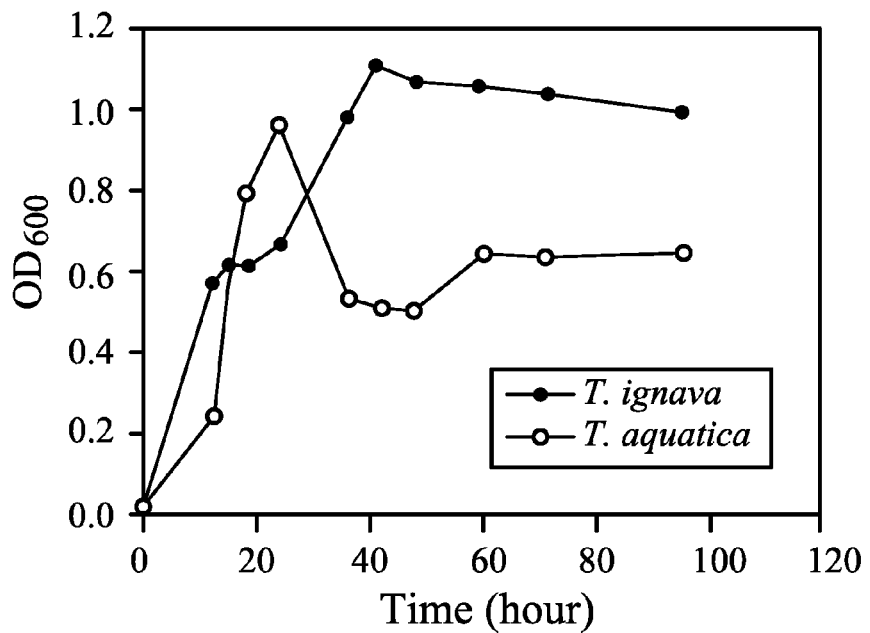
FIG. 16A and FIG. 16B respectively show the optical densities ($OD_{600}$) and protein concentrations of the *Tepidimonas ignava* SPS-1037 suspension and *Tepidimonas aquatica* CLN-1 suspension determined at different points in time at a condition of culturing *Tepidimonas fonticaldi* sp. nov. KCTC 12528BP with the culturing medium of the present disclosure.
Figure 16B:
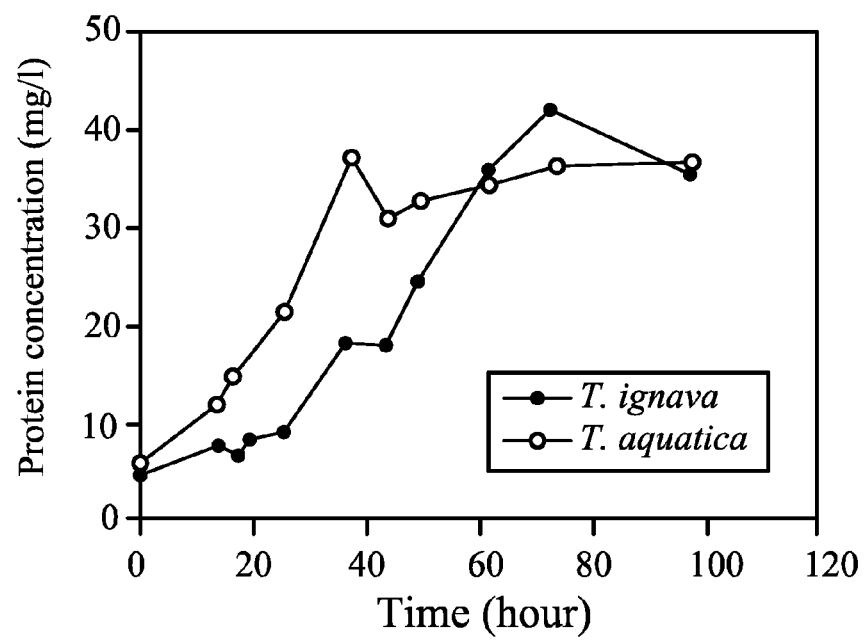

FIG. 16A and FIG. 16B respectively show the optical densities ($OD_{600}$) and protein concentrations of the *Tepidimonas ignava* SPS-1037 suspension and *Tepidimonas aquatica* CLN-1 suspension determined at different time points at a condition of culturing *Tepidimonas fonticaldi* sp. nov. KCTC 12528BP with the culturing medium of the present disclosure, According to FIG. 16A and FIG. 16B, it is known that the culturing medium of the present disclosure enables *Tepidimonas ignava* SPS-1037 and *Tepidimonas aquatica* CLN-1 to grow and produce protein.

Based on the preceding, it is understood that the culturing medium of the present disclosure is suitable for culturing various bacteria of genus *Tepidimonas*.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A culturing medium for culturing a bacterium of genus *Tepidimonas*, comprising:
   a carbon source which is acetate;
   a nitrogen source which is ammonium sulfate (($NH_4)_2SO_4$);
   a phosphate;
   magnesium chloride ($MgCl_2$);
   a yeast extract; and
   trace elements,
   wherein the content of the acetate is about 0.2 g/L-5 g/L, the content of the ammonium sulfate is about 0.4 g/L-3 g/L, the content of the phosphate is about 1 g/L-12 g/L, the content of the $MgCl_2$ is about 0.01 g/L-0.5 g/L, the content of the yeast extract is about 0.2 g/L-5 g/L, and the content of the trace elements is about 0.01 g/L-0.3 g/L.

2. The culturing medium for culturing a bacterium of genus *Tepidimonas* as claimed in claim 1, wherein the phosphate comprises disodium hydrogen phosphate ($Na_2HPO_4$) and dipotassium phosphate ($K_2HPO_4$).

3. The culturing medium for culturing a bacterium of genus *Tepidimonas* as claimed in claim 1, wherein the phosphate is dipotassium phosphate ($K_2HPO_4$).

4. The culturing medium for culturing a bacterium of genus *Tepidimonas* as claimed in claim 3, further comprising sodium bicarbonate ($NaHCO_3$).

5. The culturing medium for culturing a bacterium of genus *Tepidimonas* as claimed in claim 1, wherein the trace elements comprises zinc (Zn), manganese (Mn), boron (B), cobalt (Co), copper (Cu), nickel (Ni) and molybdenum (Mo).

6. The culturing medium for culturing a bacterium of genus *Tepidimonas* as claimed in claim 1, wherein the bacterium of genus *Tepidimonas* comprises *Tepidimonas fonticaldi*, *Tepidimonas ignava*, *Tepidimonas aquatic* or *Tepidimonas taiwanesis*.

7. The culturing medium for culturing a bacterium of genus *Tepidimonas* as claimed in claim 1, wherein the bacterium of genus *Tepidimonas* is *Tepidimonas fonticaldi*.

8. The culturing medium for culturing a bacterium of genus *Tepidimonas* as claimed in claim 7, wherein the *Tepidimonas fonticaldi* is *Tepidimonas fonticaldi* sp. nov. KCTC 12528BP.

9. The culturing medium for culturing a bacterium of genus *Tepidimonas* as claimed in claim 1, wherein in the culturing medium for culturing a bacterium of genus *Tepidimonas*, the carbon-nitrogen weight ratio of the carbon source to the nitrogen source is about 1-20.

10. The culturing medium for culturing a bacterium of genus *Tepidimonas* as claimed in claim 9, wherein in the culturing medium for culturing a bacterium of genus *Tepidimonas*, the carbon-nitrogen weight ratio of the carbon source to the nitrogen source is 11.

11. A method for culturing a bacterium of genus *Tepidimonas*, comprising:
culturing a bacterium of genus *Tepidimonas* with the culturing medium of claim 1.

12. The method for culturing a bacterium of genus *Tepidimonas* as claimed in claim 11, wherein the bacterium of genus *Tepidimonas* is cultured at about 30-70° C.

13. The method for culturing a bacterium of genus *Tepidimonas* as claimed in claim 12, wherein the bacterium of genus *Tepidimonas* is cultured at about 30-60° C.

14. The method for culturing a bacterium of genus *Tepidimonas* as claimed in claim 13, wherein the bacterium of genus *Tepidimonas* is cultured at about 55° C.

15. The method for culturing a bacterium of genus *Tepidimonas* as claimed in claim 11, wherein the bacterium of genus *Tepidimonas* is cultured at pH 5-pH 9.

16. The method for culturing a bacterium of genus *Tepidimonas* as claimed in claim 15, wherein the bacterium of genus *Tepidimonas* is cultured at pH 6-pH 9.

17. The method for culturing a bacterium of genus *Tepidimonas* as claimed in claim 16, wherein the bacterium of genus *Tepidimonas* is cultured at pH 7 or pH 8.

18. The method for culturing a bacterium of genus *Tepidimonas* as claimed in claim 11, wherein the bacterium of genus *Tepidimonas* is cultured under a stirring rate of about 0-500 rpm.

19. The method for culturing a bacterium of genus *Tepidimonas* as claimed in claim 18, wherein the bacterium of genus *Tepidimonas* is cultured under a stirring rate of about 0-200 rpm.

20. The method for culturing a bacterium of genus *Tepidimonas* as claimed in claim 19, wherein the bacterium of genus *Tepidimonas* is cultured under a stirring rate of about 200 rpm.

21. The method for culturing a bacterium of genus *Tepidimonas* as claimed in claim 11, wherein in the culturing medium for culturing a bacterium of genus *Tepidimonas*, the phosphate comprises disodium hydrogen phosphate ($Na_2HPO_4$) and dipotassium phosphate ($K_2HPO_4$).

22. The method for culturing a bacterium of genus *Tepidimonas* as claimed in claim 11, wherein in the culturing medium for culturing a bacterium of genus *Tepidimonas*, the phosphate is dipotassium phosphate ($K_2HPO_4$).

23. The method for culturing a bacterium of genus *Tepidimonas* as claimed in claim 22, wherein the culturing medium for culturing a bacterium of genus *Tepidimonas* further comprises sodium bicarbonate ($NaHCO_3$).

24. The method for culturing a bacterium of genus *Tepidimonas* as claimed in claim 11, wherein in the culturing medium for culturing a bacterium of genus *Tepidimonas*, the trace elements comprises zinc (Zn), manganese (Mn), boron (B), cobalt (Co), copper (Cu), nickel (Ni) and molybdenum (Mo).

25. The method for culturing a bacterium of genus *Tepidimonas* as claimed in claim 11, wherein the bacterium of genus *Tepidimonas* comprises *Tepidimonas fonticaldi, Tepidimonas ignava, Tepidimonas aquatic* or *Tepidimonas taiwanesis*.

26. The method for culturing a bacterium of genus *Tepidimonas* as claimed in claim 11, wherein the bacterium of genus *Tepidimonas* is *Tepidimonas fonticaldi*.

27. The method for culturing a bacterium of genus *Tepidimonas* as claimed in claim 26, wherein the *Tepidimonas fonticaldi* is *Tepidimonas fonticaldi* sp. nov. KCTC 12528BP.

28. The method for culturing a bacterium of genus *Tepidimonas* as claimed in claim 11, wherein in the culturing medium for culturing a bacterium of genus *Tepidimonas*, the carbon-nitrogen weight ratio of the carbon source to the nitrogen source is about 1-20.

29. The method for culturing a bacterium of genus *Tepidimonas* as claimed in claim 28, wherein in the culturing medium for culturing a bacterium of genus *Tepidimonas*, the carbon-nitrogen weight ratio of the carbon source to the nitrogen source is 11.

* * * * *